(12) United States Patent
Clerc et al.

(10) Patent No.: US 9,675,473 B2
(45) Date of Patent: Jun. 13, 2017

(54) STENT WITH ANTI-MIGRATION FEATURES

(71) Applicant: Boston Scientific Scimed. Inc., Maple Grove, MN (US)

(72) Inventors: Claude Clerc, Marlborough, MA (US); Brian Joseph Tischler, New Brighton, MA (US); Mark McPhail, Maple Grove, MN (US); Daniel Ross, Watertown, MN (US); Burns P. Doran, Monticello, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 639 days.

(21) Appl. No.: 13/722,313

(22) Filed: Dec. 20, 2012

(65) Prior Publication Data
US 2013/0172983 A1 Jul. 4, 2013

Related U.S. Application Data

(60) Provisional application No. 61/581,444, filed on Dec. 29, 2011.

(51) Int. Cl.
*A61F 2/82* (2013.01)
*A61F 2/848* (2013.01)
*A61F 2/915* (2013.01)

(52) U.S. Cl.
CPC ............ *A61F 2/82* (2013.01); *A61F 2/848* (2013.01); *A61F 2/915* (2013.01); *A61F 2002/8483* (2013.01); *A61F 2002/91525* (2013.01); *A61F 2002/91533* (2013.01); *A61F 2002/91558* (2013.01); *A61F 2002/91575* (2013.01);
(Continued)

(58) Field of Classification Search
CPC .. A61F 2/82; A61F 2/848; A61F 2/915; A61F 2220/0016; A61F 2250/0039; A61F 2002/91575; A61F 2002/91533; A61F 2002/91558; A61F 2002/91525; A61F 2002/8483
See application file for complete search history.

(56) References Cited

U.S. PATENT DOCUMENTS 5,591,197 A * 1/1997 Orth et al. ............. 623/1.16
7,582,111 B2 * 9/2009 Krolik et al. .......... 623/1.32
8,292,946 B2 10/2012 Thistle et al.
(Continued)

FOREIGN PATENT DOCUMENTS

EP 0732088 9/1996
WO 0027310 5/2000
(Continued)

OTHER PUBLICATIONS

Bolliger et al., "Evaluation of a New Self-expandable Silicone Stent in an Experimental Tracheal Stenosis," Chest /115 / 2 / Feb. 1999, pp. 496-501.
(Continued)

Primary Examiner — Anh Dang
(74) Attorney, Agent, or Firm — Seager, Tufte & Wickhem, LLP

(57) ABSTRACT

A stent has a first end region, a middle region, and a second end region, each region including a plurality of strut columns. The stent includes at least one barb. Each barb in an expanded state is at an angle relative to the outer surface of the stent.

12 Claims, 35 Drawing Sheets

(52) U.S. Cl.
CPC .............. *A61F 2220/0016* (2013.01); *A61F 2250/0039* (2013.01)

(56) References Cited

U.S. PATENT DOCUMENTS

| | | | |
|---|---|---|---|
| 2003/0109887 A1* | 6/2003 | Galdonik et al. | 606/108 |
| 2004/0044400 A1* | 3/2004 | Cheng et al. | 623/1.16 |
| 2005/0043784 A1 | 2/2005 | Yampolsky et al. | |
| 2005/0182483 A1* | 8/2005 | Osborne et al. | 623/1.24 |
| 2007/0093888 A1 | 4/2007 | Thistle et al. | |
| 2008/0065194 A1 | 3/2008 | Dakin et al. | |
| 2008/0249598 A1 | 10/2008 | Sherry | |
| 2009/0187240 A1 | 7/2009 | Clerc et al. | |
| 2011/0106237 A1 | 5/2011 | Bonsignore et al. | |
| 2013/0018452 A1 | 1/2013 | Weitzner et al. | |

FOREIGN PATENT DOCUMENTS

| | | |
|---|---|---|
| WO | 03053288 | 7/2003 |
| WO | 2011029631 | 3/2011 |

OTHER PUBLICATIONS

Bolliger et al., "Use of Studded Polyflex™ Stents in Patients with Neoplastic Obstructions of the Central Airways," Respiration 2004; 71: pp. 83-87.

Kim et al., "Tracheal Stricture and Fistula: Management With a Barbed Silicone-Covered Retrievable Expandable Nitinol Stent," AJR: 194, Feb. 2010.

* cited by examiner

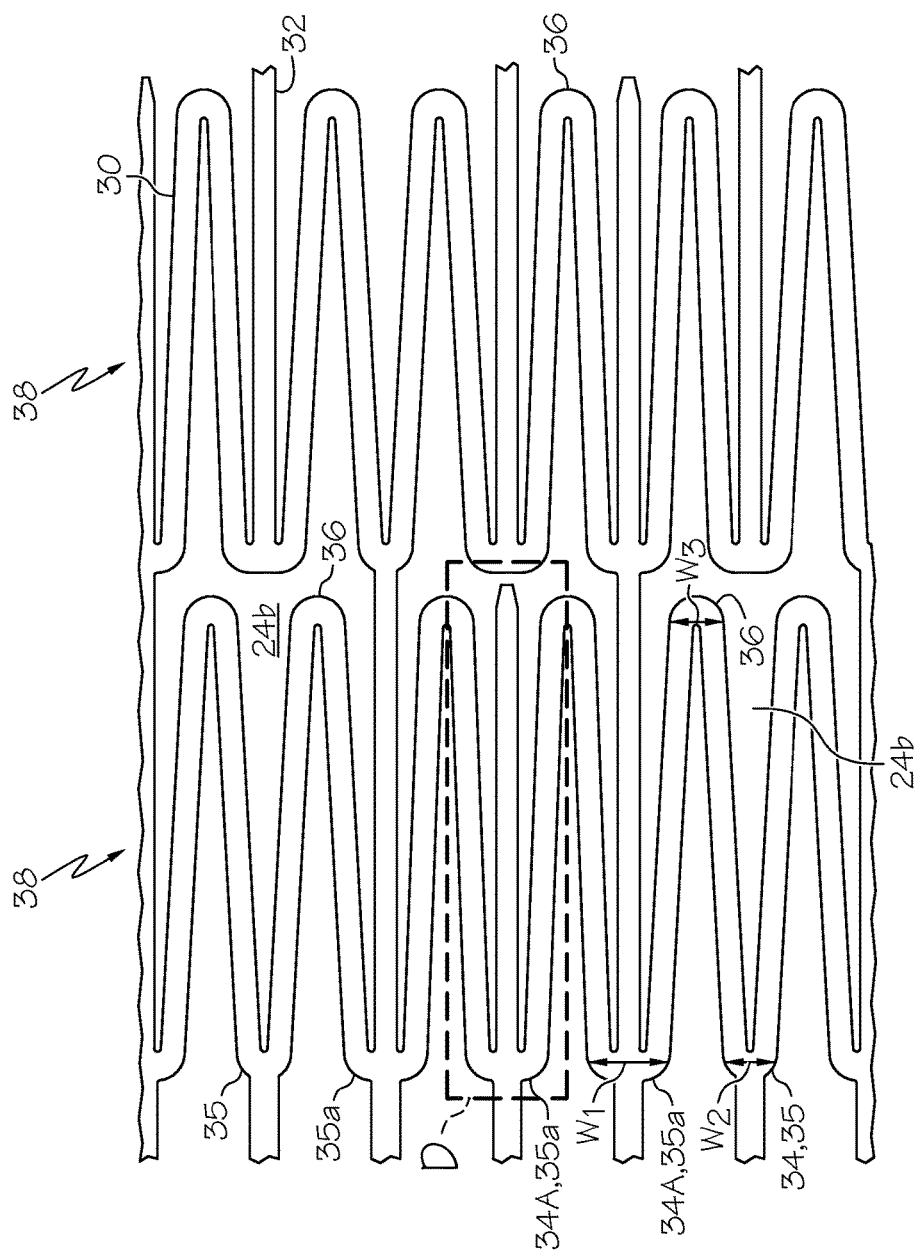

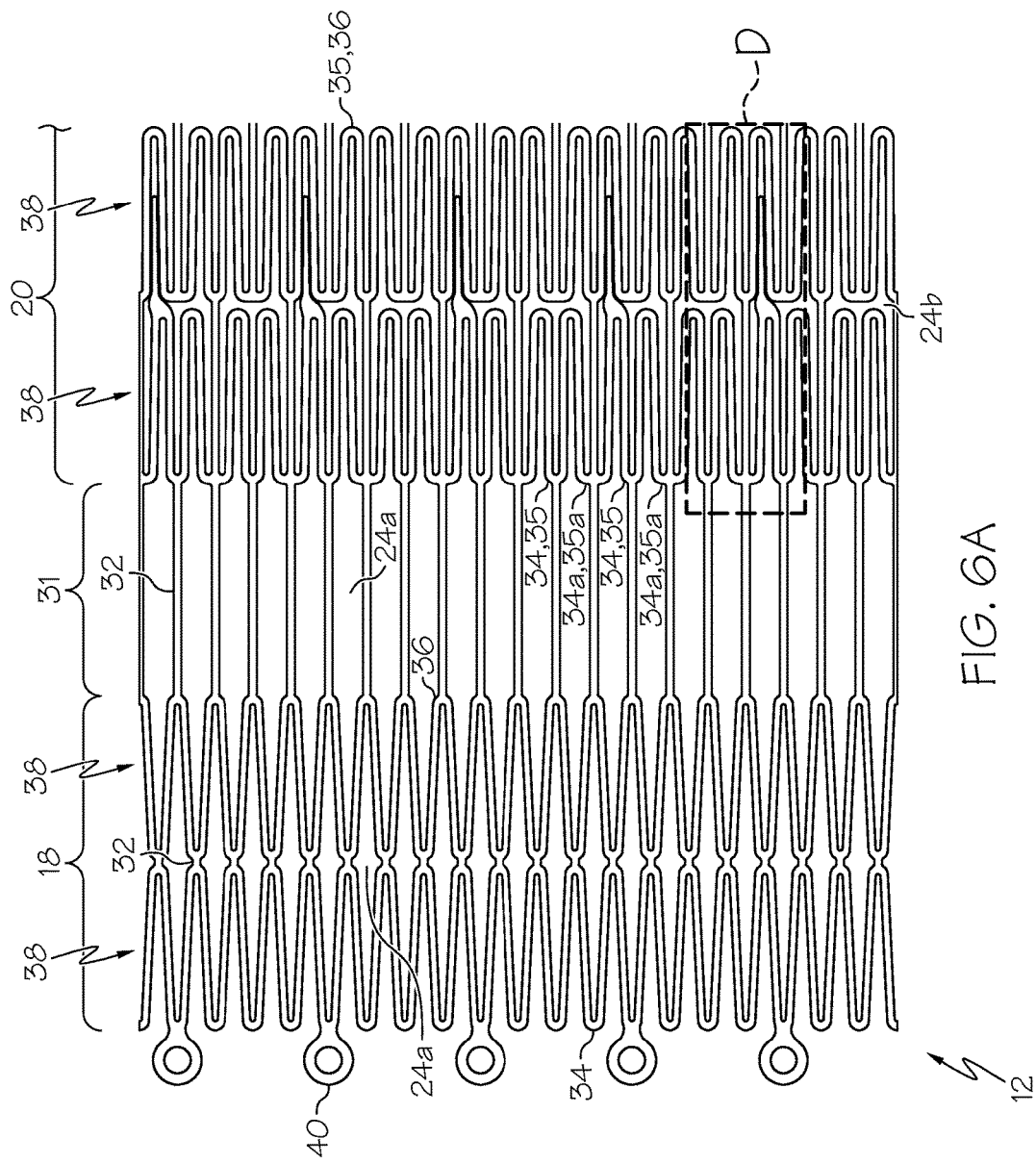

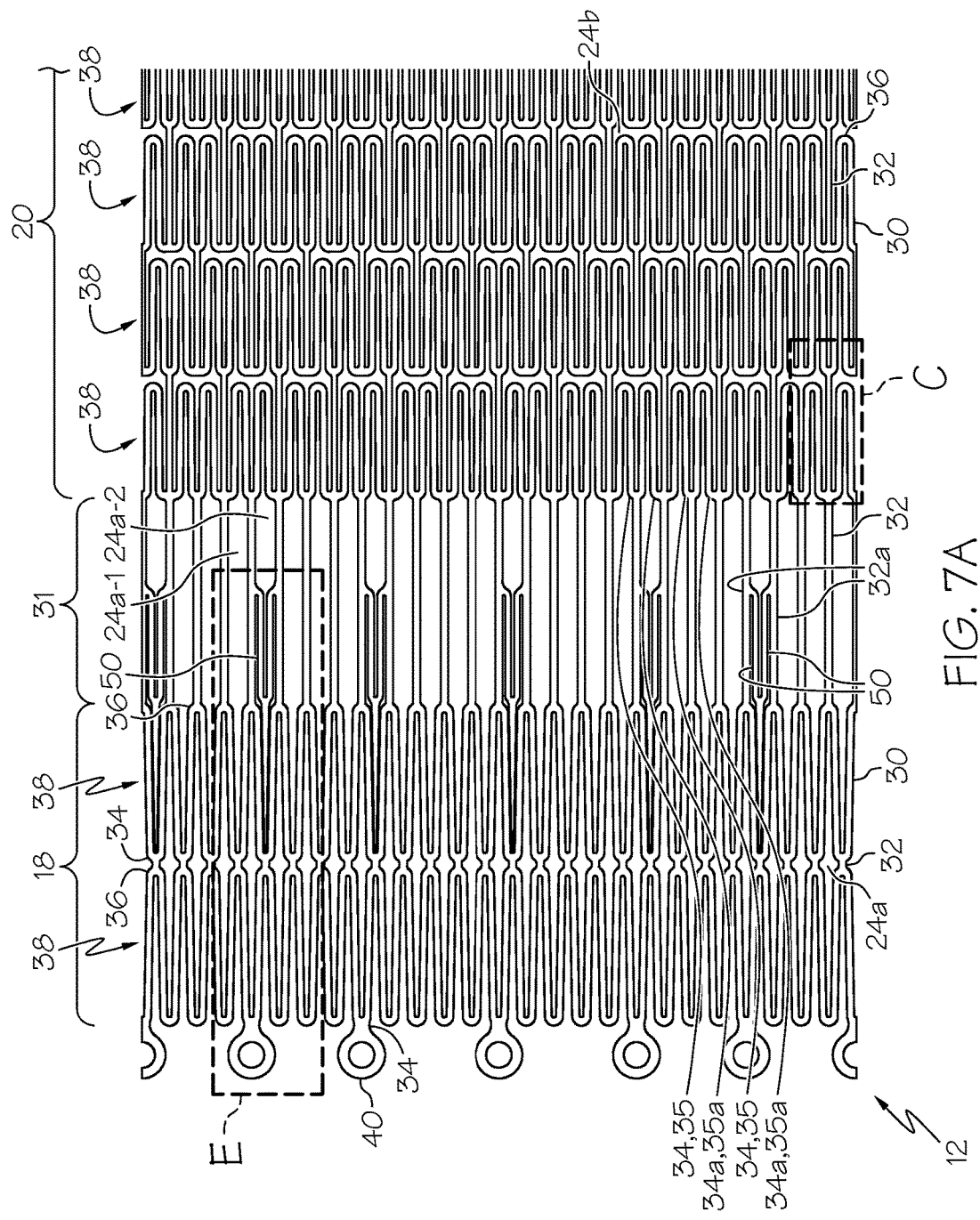

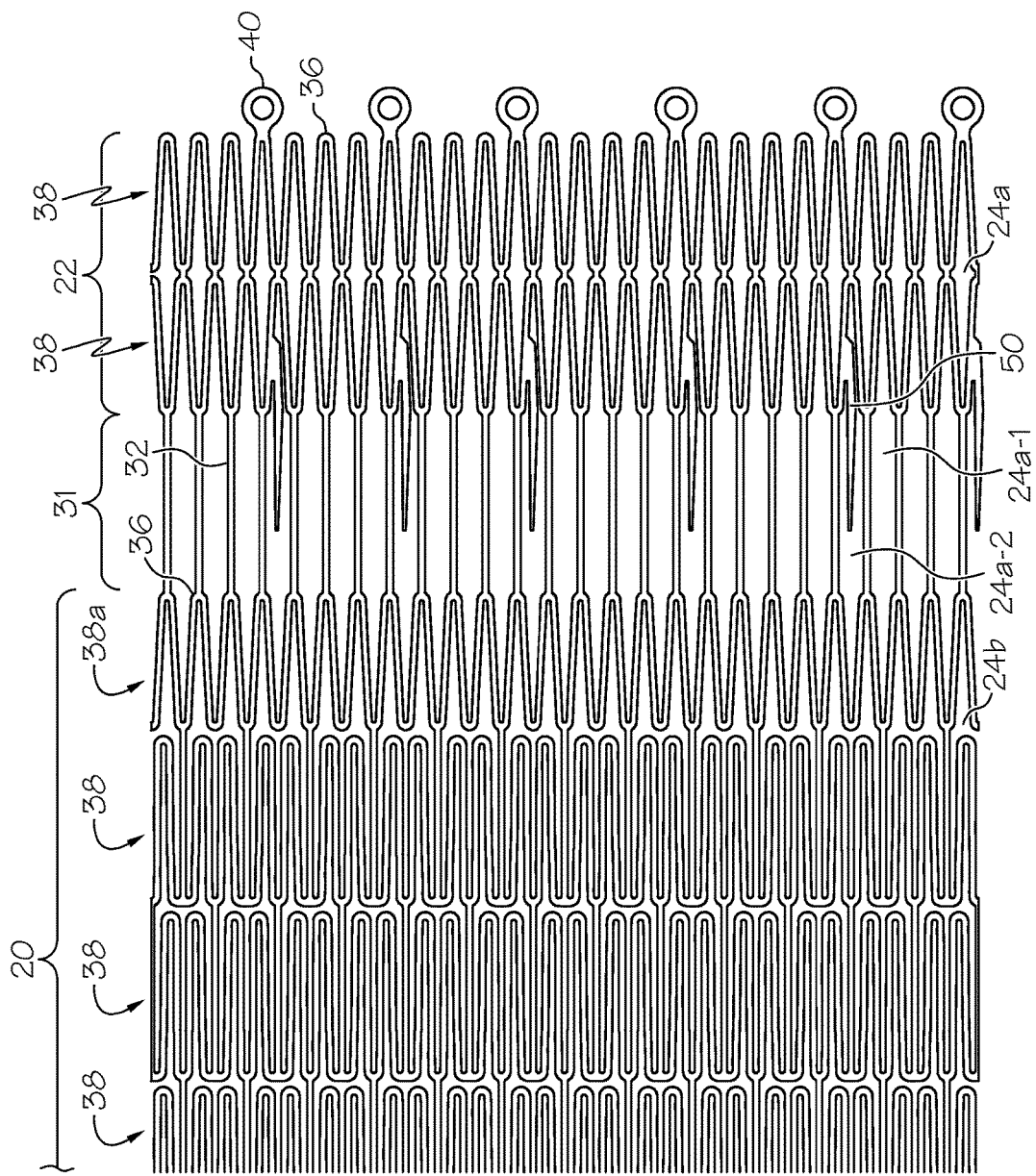

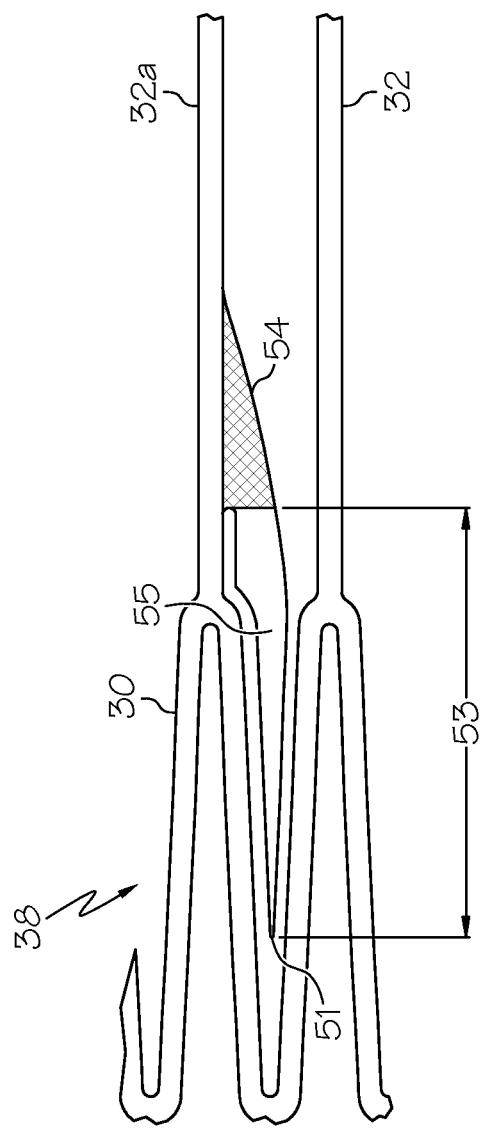

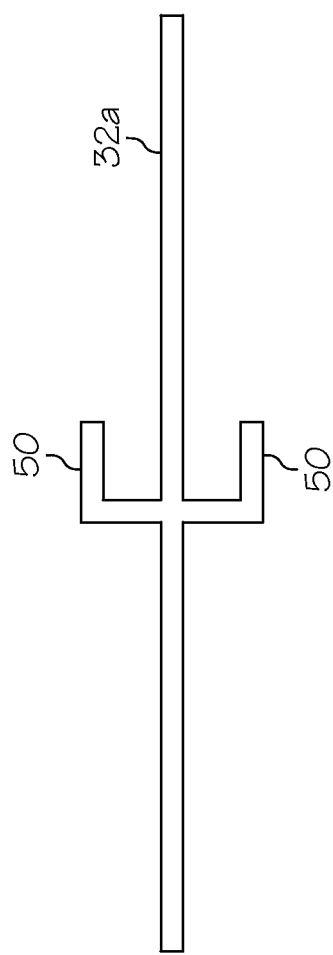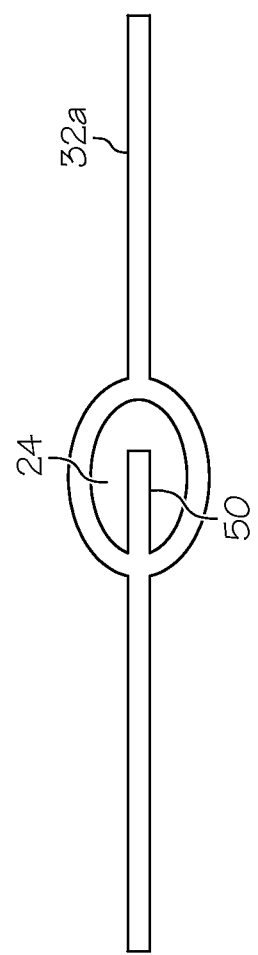

STENT WITH ANTI-MIGRATION FEATURES

CROSS-REFERENCE TO RELATED APPLICATIONS

This application claims priority to U.S. Application No. 61/581,444 filed Dec. 29, 2011.

STATEMENT REGARDING FEDERALLY SPONSORED RESEARCH

Not Applicable

BACKGROUND OF THE INVENTION

Stents may be implanted in a variety of body lumens or vessels such as within the vascular system, urinary tracts, gastrointestinal tracts, fallopian tubes, coronary vessels, secondary vessels, airways, structural heart (valve frame), etc. They may be self-expanding, expanded by an internal radial force, such as when mounted on a balloon, or a combination of self-expanding and balloon expandable (hybrid expandable). Some stents are partially or fully covered. Migration of the stent from its initial site of implantation can be undesirable.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

At least one embodiment includes a stent that has a first end region, a middle region, a second end region, and a plurality of connectors. In some embodiments, the stent includes at least one barb or fin that have an expanded state where the barb/fin is at an angle relative to the outer surface of the stent.

These and other embodiments which characterize the invention are pointed out with particularity in the claims annexed hereto and forming a part hereof. However, for further understanding of the invention reference can be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

FIGS. 1A-D are schematic illustrations of different states of a stent described herein.

FIG. 2C is an enlarged portion of the stent in FIG. 2.

FIG. 6A is an enlarged view of the first part of the stent in FIG. 6.

FIG. 7A is an enlarged view of the first part of the stent in FIG. 7.

FIG. 8B is an enlarged view of the second part of the stent in FIG. 8.

FIG. 9C is an enlarged portion of the stent in FIG. 9

FIGS. 10-12 are schematics of a connector with a barb.

DETAILED DESCRIPTION OF THE INVENTION

Figure 1A:
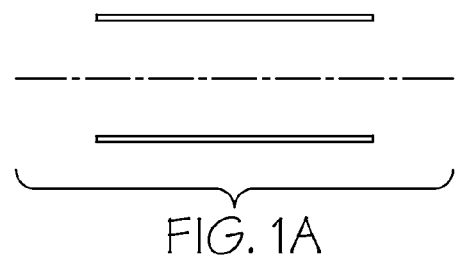
Figure 1B:
Figure 1C:
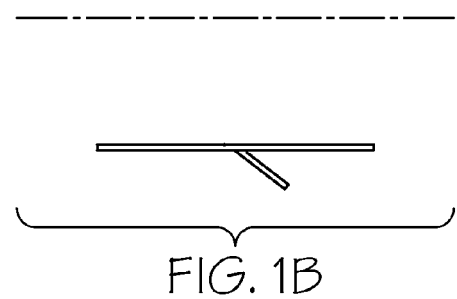
Figure 1D:
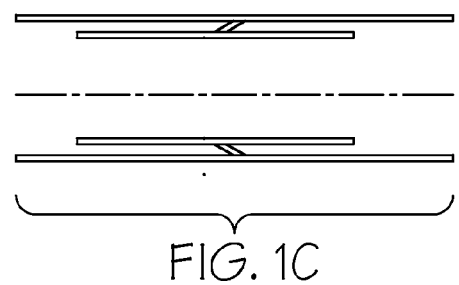

While this invention may be embodied in many different forms, there are described in detail herein specific embodiments of the invention. This description is an exemplification of the principles of the invention and is not intended to limit the invention to the particular embodiments illustrated. Furthermore, reference to a particular figure as showing a detail described herein does not indicate that other figures do not show the same detail.

For the purposes of this disclosure, like reference numerals in the figures shall refer to like features unless otherwise indicated. Additionally reference to a primary reference numeral such as 1, includes secondary reference numerals such as 1a unless explicitly stated otherwise and reference to FIG. 2 includes reference to all the view of FIG. 2, e.g. FIGS. 2A-F.

As used in this application, "approximately" means very similar; nearly and thus includes slight deviations.

A stent as described herein has several states, an "as cut state," followed by a "parent or fully expanded state," followed by a "crimped state," followed by a "deployed state." As used in this application, a stent is in an "as cut state" after laser cutting and prior to expansion; a stent is in the "parent state" or "fully expanded state" after expansion from the as cut state and heat treated (as manufactured); a stent is in a "crimped state" when positioned on a delivery device; and a stent is in the "deployed state" when it is deployed in a body lumen. These states are shown schematically in FIG. 1. As shown in FIG. 1 the diameter of the stent in an as cut state is different than the diameter of the stent in the parent state and the diameter of the deployed state is different than the diameter of the parent state with the diameter in the parent state being greater than the diameter of the as-cut state.

As used in this application, an "inner surface" of the stent is a surface that defines the lumen of the stent 10 and the "outer surface" of the stent is opposite the inner surface.

As used in this application, a "strut column," "serpentine ring," or "serpentine band," comprises a plurality of struts 30 interconnected by a plurality of turns 34, 34a, 35, 35a, and 36. Each turn 34, 34a, 35, 35a, and 36 extends between two struts 30 and each strut 30 extends from two turns 34, 34a, 35, 35a, and 36. In some embodiments, the strut column is closed. This can be seen from the figures, each strut column is closed. As used in this application "closed" means that the struts and turns of a strut column form a continuous pathway that extends about the entire circumference of the stent.

As used in this application, adjacent strut columns that are "out of phase" have turns that are circumferentially aligned and facing opposite directions; and adjacent strut columns that are "in phase" have turns that are circumferentially aligned and facing the same direction.

As used in this application, a "turn" 35 refers to either a "peak" 34 which is a turn 35 that extends towards the first end 12 of the stent or a "valley" 36 which is a turn 35 extends towards the second end 14 of the stent. As used in this application, a "chevron turn" 35a is a turn 35 that has a circumferential width ($W_1$) greater than the circumferential width ($W_2$) of the other turns 35, as can be seen for example in FIG. 3. Thus, a chevron turn 35a can be described as wide turns and the other turns 35 can be described as narrow turns.

As used in this application a "peak to peak connector" 32 extends between a peak 34 on one strut column 38 to a peak 34 on another strut column 38; a "valley to valley connector" 32 extends between a valley 36 on one strut column 38 to a valley 36 on another strut column 38; and a "peak to valley connector" 32 extends between a peak 34 on one strut column 38 to a valley 36 on another strut column 38 or vice versa. It is noted that whether a connector is a peak to peak connector or a valley to valley connector is dependent on the orientation of the stent. Thus, when the stent is oriented in one direction a particular connector can be a peak to peak connector, whereas when the stent is oriented in the opposite direction the connector is a valley to valley connector.

Figure 4:
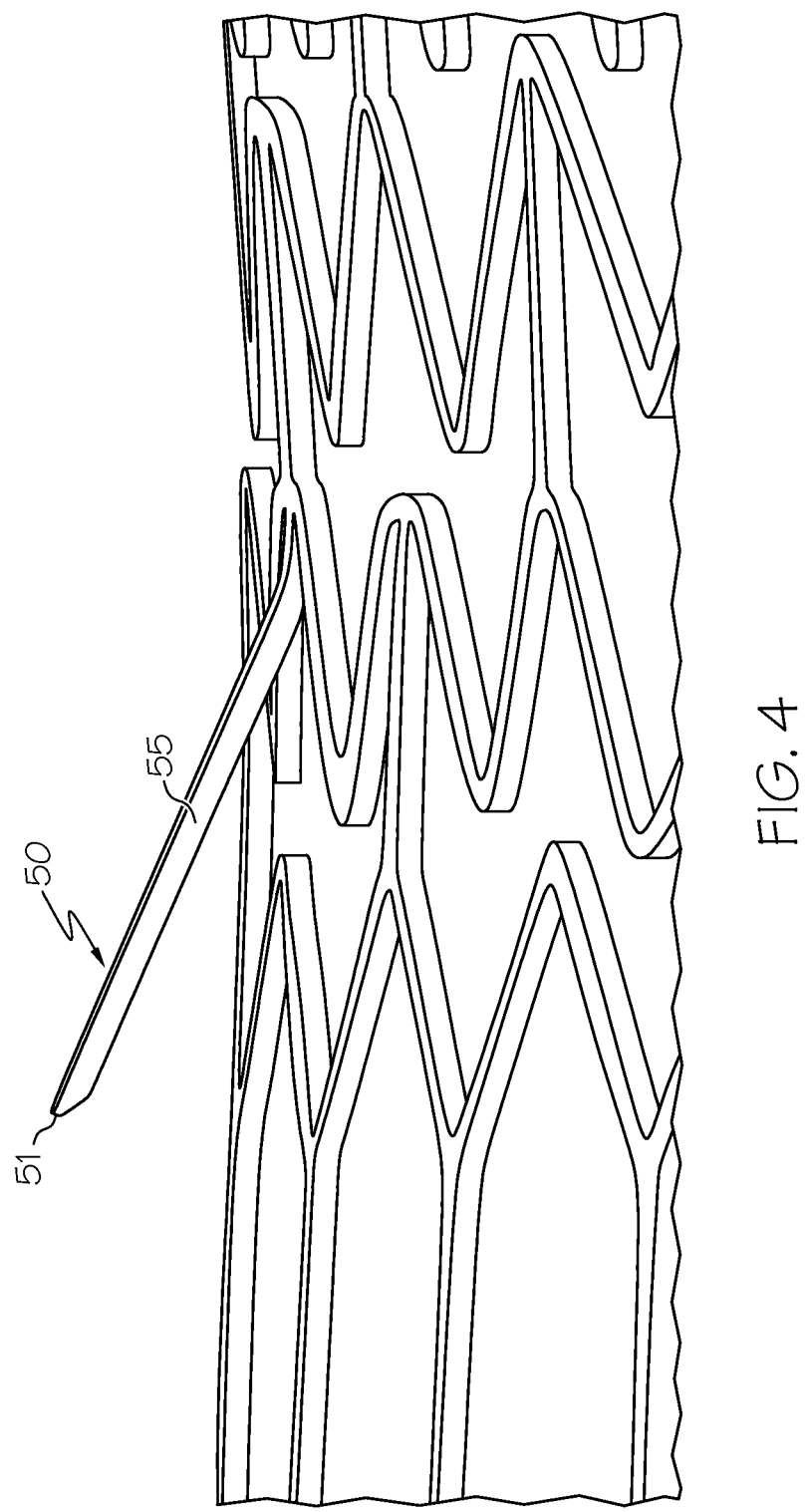
FIG. 4 is a schematic side profile view of a barb of the stent in FIG. 3 in an expanded state.
Figure 13:
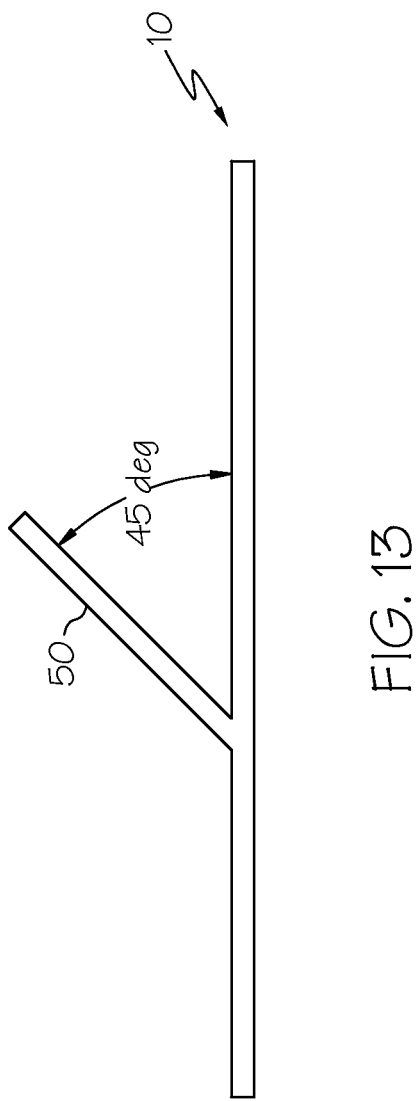
FIG. 13 is a schematic side profile view of a barb in an expanded state.

As used in this application, a barb or fin 50 is in an "expanded or parent state" when at least a portion of the barb/fin 50 is at an angle relative to the outer surface of the tubular stent 10 and a barb/fin 50 is in an "unexpanded state" when the barb/fin 50 forms a part of the tubular wall of the stent 10 in the as cut state. The barb is in the unexpanded state when the stent is in the as cut state. The barb is in the expanded state when the stent is in the parent state and when the stent is in the deployed state. The barb 50 in an expanded state is at an angle relative to the longitudinal axis of the stent 10 and/or relative to the outer surface of the stent. FIGS. 4 and 13 show a barb in the expanded state.

Figure 2:
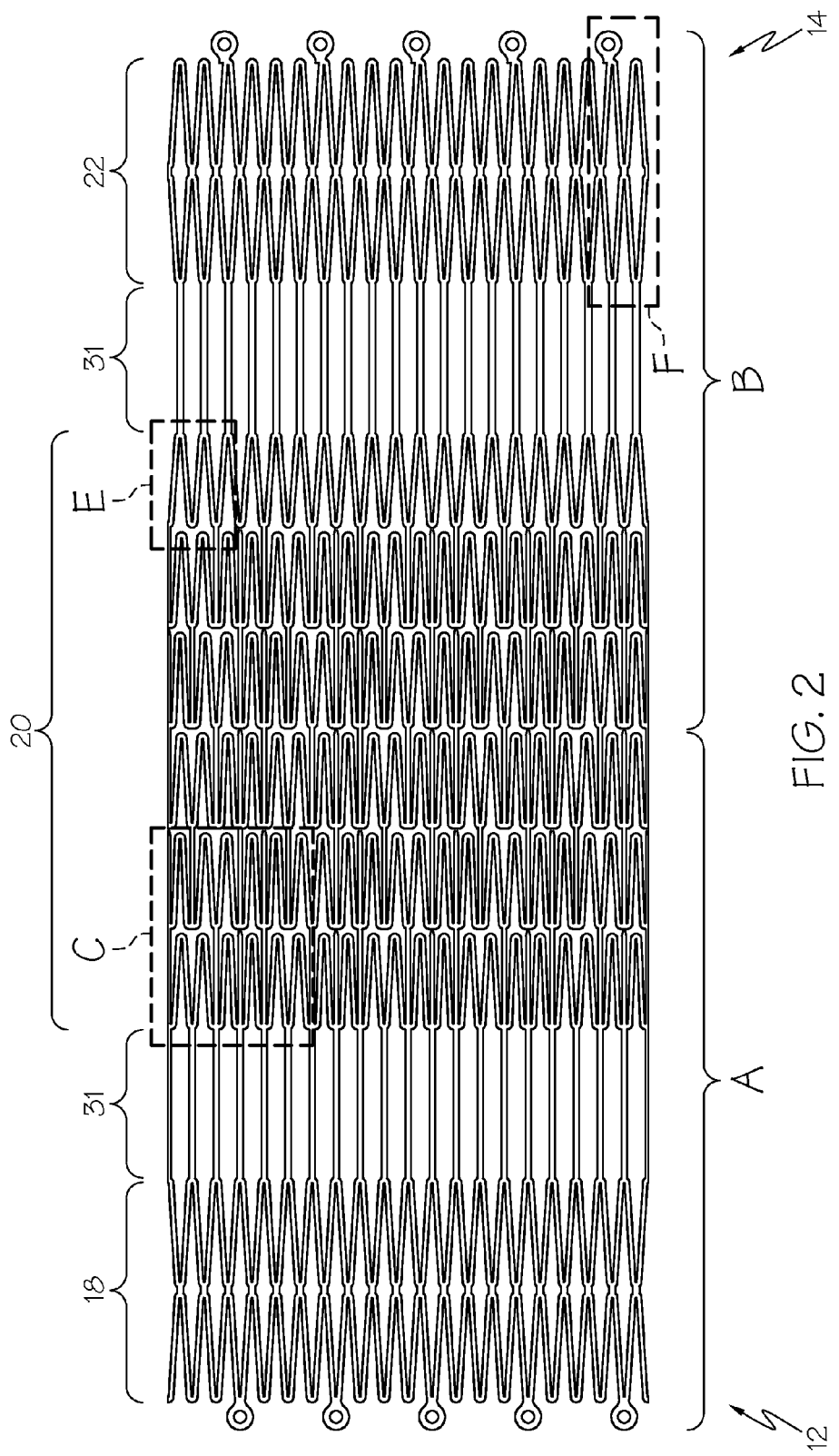
FIG. 2 is a flat plan view of a stent.
Figure 2A:
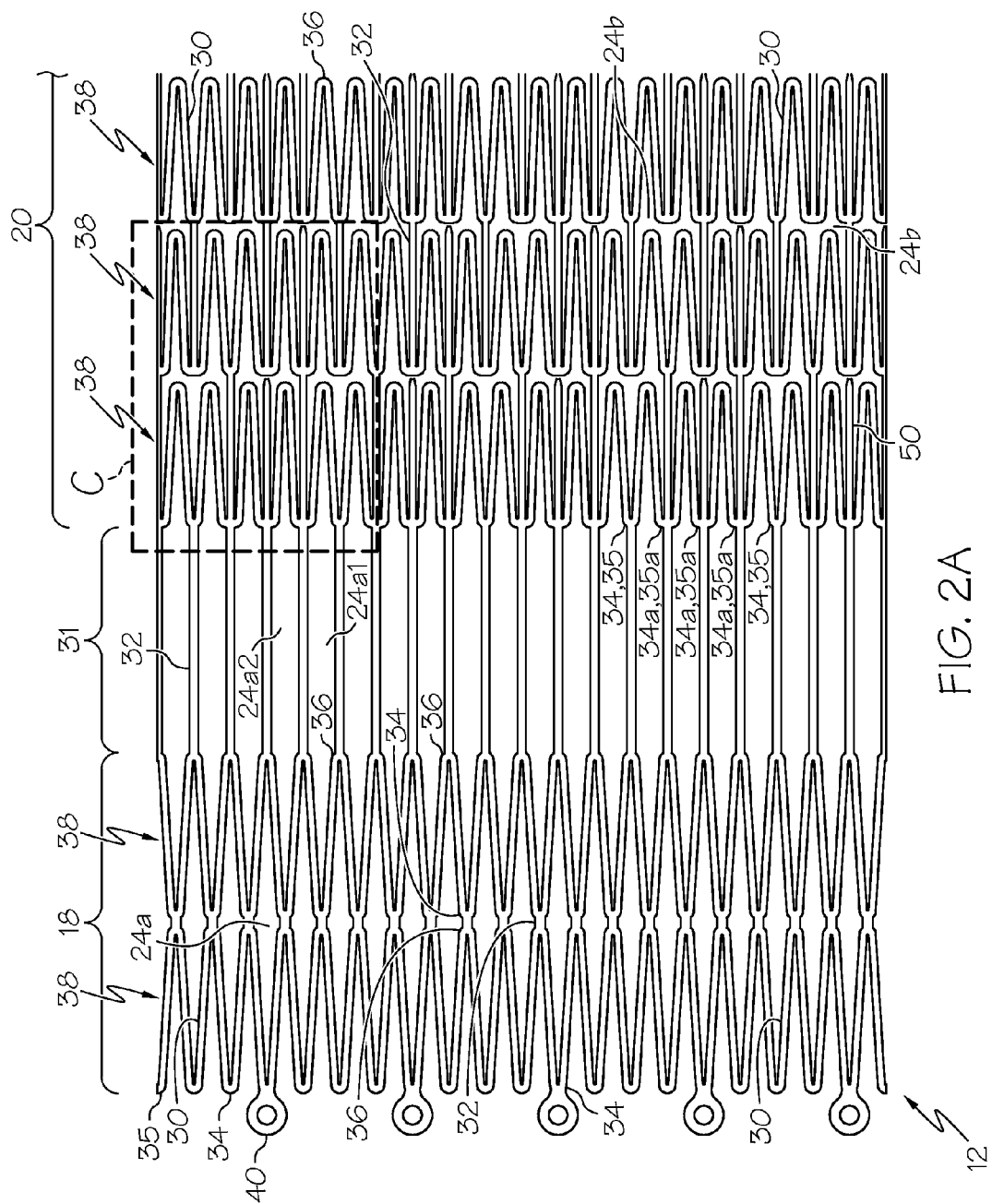
FIG. 2A is an enlarged view of the first part of the stent in FIG. 2.
Figure 2B:
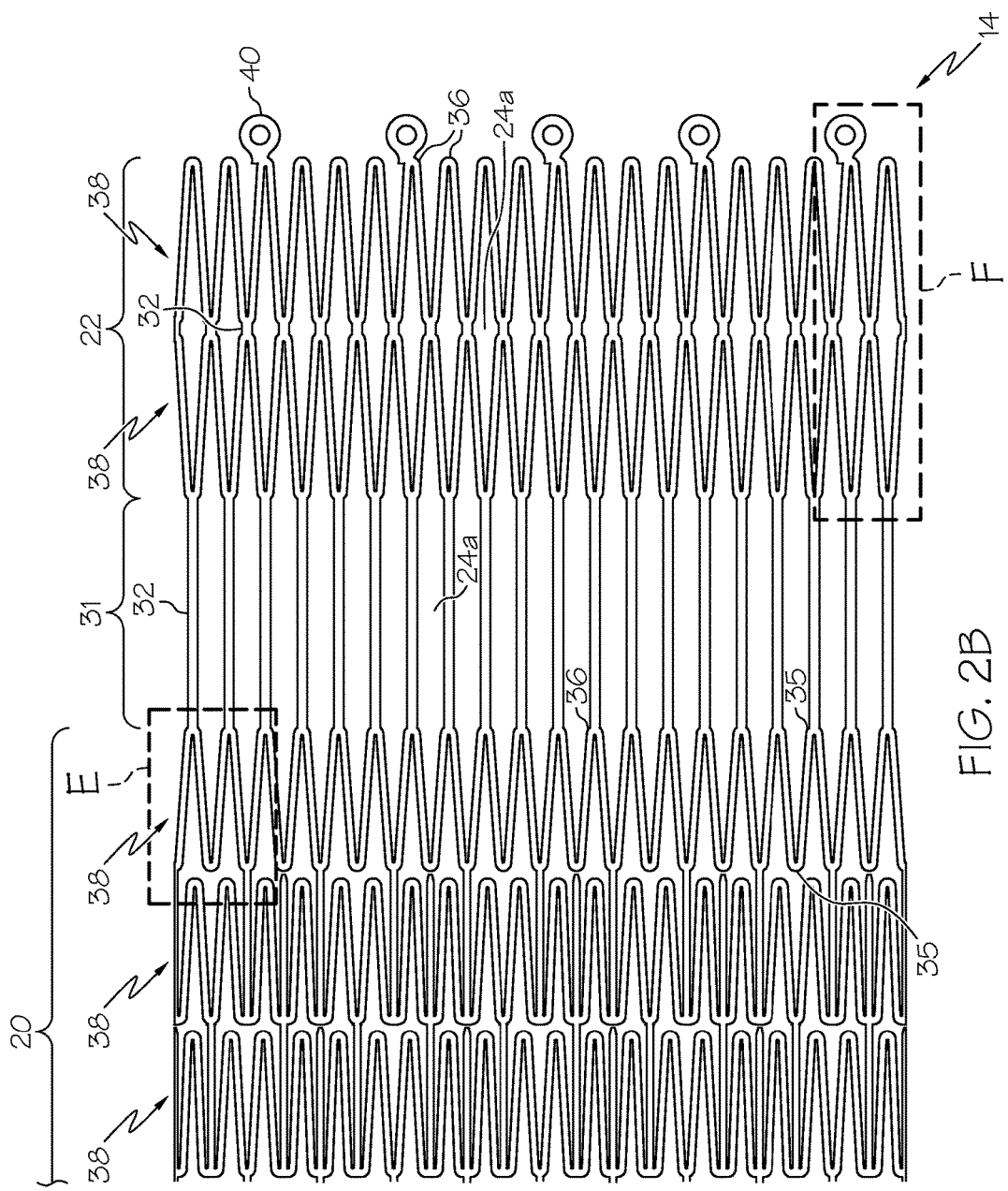
FIG. 2B is an enlarged view of the second part of the stent in FIG. 2.
Figure 2D:
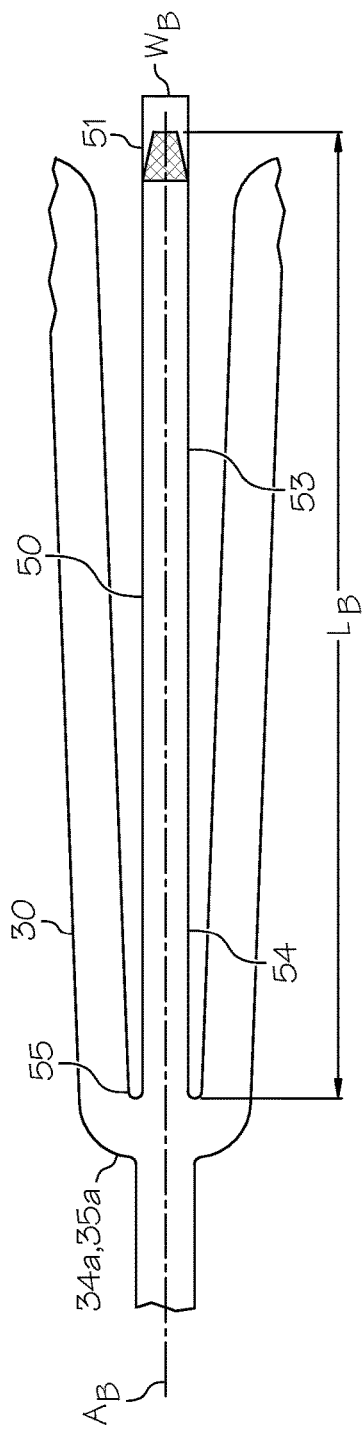
FIG. 2D is an enlarged portion of FIG. 2C.
Figure 2F:
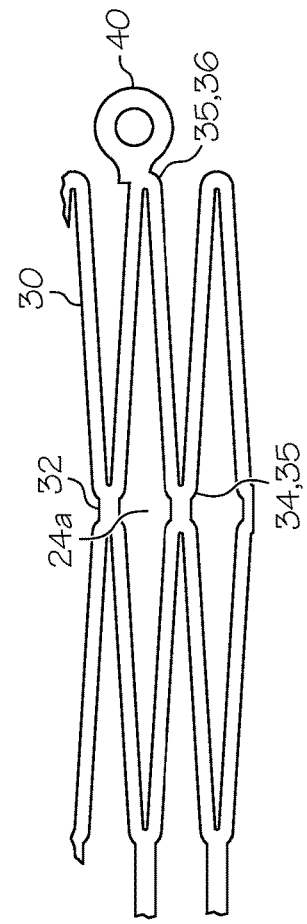
FIG. 2F is an enlarged portion of the stent in FIG. 2.
Figure 2E:
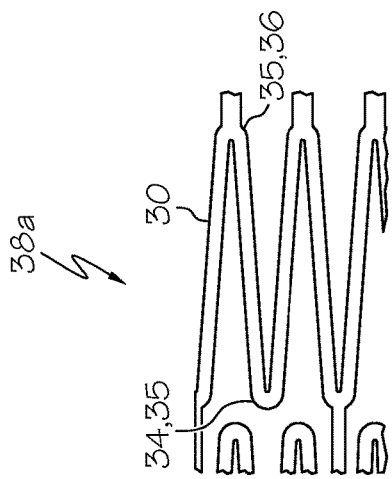
FIG. 2E is an enlarged portion of the stent in FIG. 2.
Figure 3:
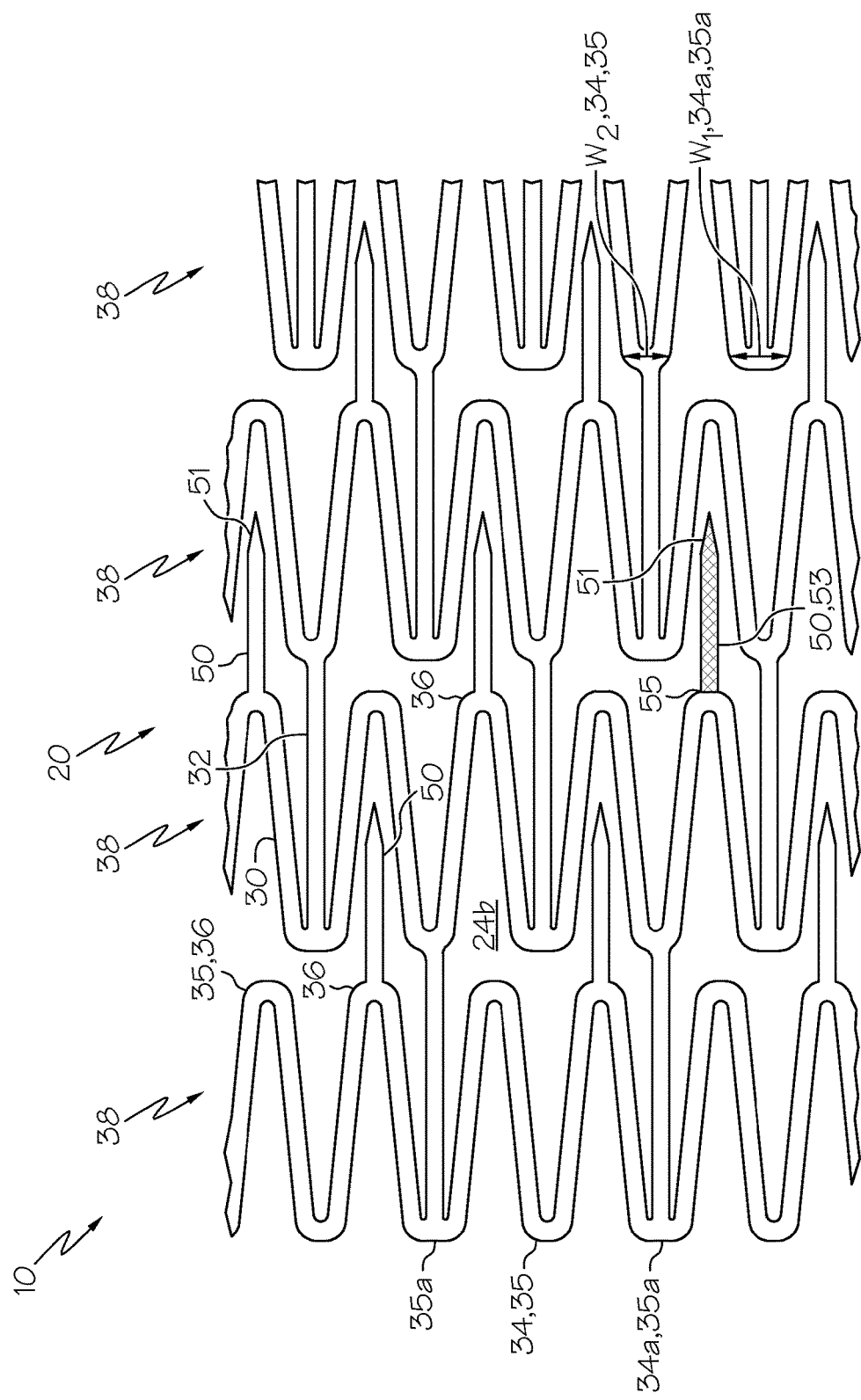
FIG. 3 is a flat plan view of a portion of a stent.

The stent and elements forming the stent have a width, length, and thickness. As used in this application, "thickness" is measured radially from the outer surface of the stent to the inner surface of the stent. FIGS. 2D and 3 illustrate how "width" (W) and "length" (L) are used in this application.

As used in this application, the terms "extending between"; "connect"; "engage" do not include "indirect" connection or engagement. Thus, for example Element B "extending between" Elements A and C extends directly between A and C with no other element between A and B or between B and C.

A. The Stent

In at least one embodiment, the stent 10 has a plurality of regions 18, 20, 22 and at least one barb 50. Exemplary patterns for the stent 10 are shown in FIGS. 2-10. Discussed below are features of the barbs 50, features of the stent 10, and features of the stent 20 with barbs 50.

A1. The Barbs

It is noted that the features of a barb 50 are not limited to the specific embodiments shown in the figures and can include mixtures of features described below. Each barb 50 has an end 55, an end region 54, a free end/tip 51, a body 53 extending from the tip 51 to the end region 54, a length ($L_B$) measured from the tip 51 to the end 55, and a width ($W_B$).

Each barb 50 has an overall configuration or shape based on the shape of the tip 51, the shape of the body, 53, and the shape of the end region 54. Thus, for example, the barbs 50 in FIGS. 2D, 3, 5D, 5E, 6D, 7E, 8C, and 9C have different overall configurations from one another.

In at least one embodiment, the barb 50 has a wall to strut ratio between 5:1 and 1:2. As used in this application, a "wall to strut ratio" is a measure of wall thickness over strut width.

In some embodiments, the barb 50 has a length ($L_B$) of 1 mm to 4 mm. In other embodiments, the barb 50 has a length ($L_B$) of 2 mm to 3 mm. In at least one embodiment, a portion of the barb 50 has a variable width. Thus, at least one region 51, 53, 54 of the barb has a width that is different from at least one other region 51, 53, 54 of the barb; at least one region of the barb has a plurality of widths along the length of the region; and combinations thereof.

Figure 14:
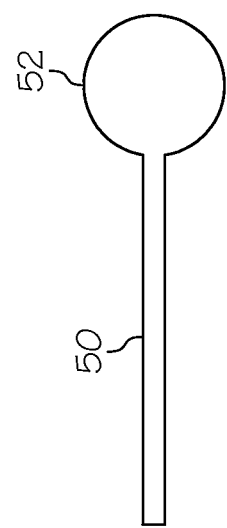
FIGS. 14-17 are schematic illustrations of a barb with FIGS. 15-17 being side profile views.

Although it is within the scope of the invention for the tip 51 of the barb to have any suitable shape, the figures show some non-limiting examples of different shapes for the tip 51 of the barb 50, such as a truncated triangle (e.g. FIG. 2D); a truncated cone tip 51 (e.g. FIG. 2D); a rounded tip 51 (e.g. FIG. 5D); a triangular tip 51 (e.g. FIG. 3); a square tip, or a tip 51 that is a ball (e.g. FIG. 14). Some of these exemplary tips 51 can be described as having a variable width.

Figure 5:
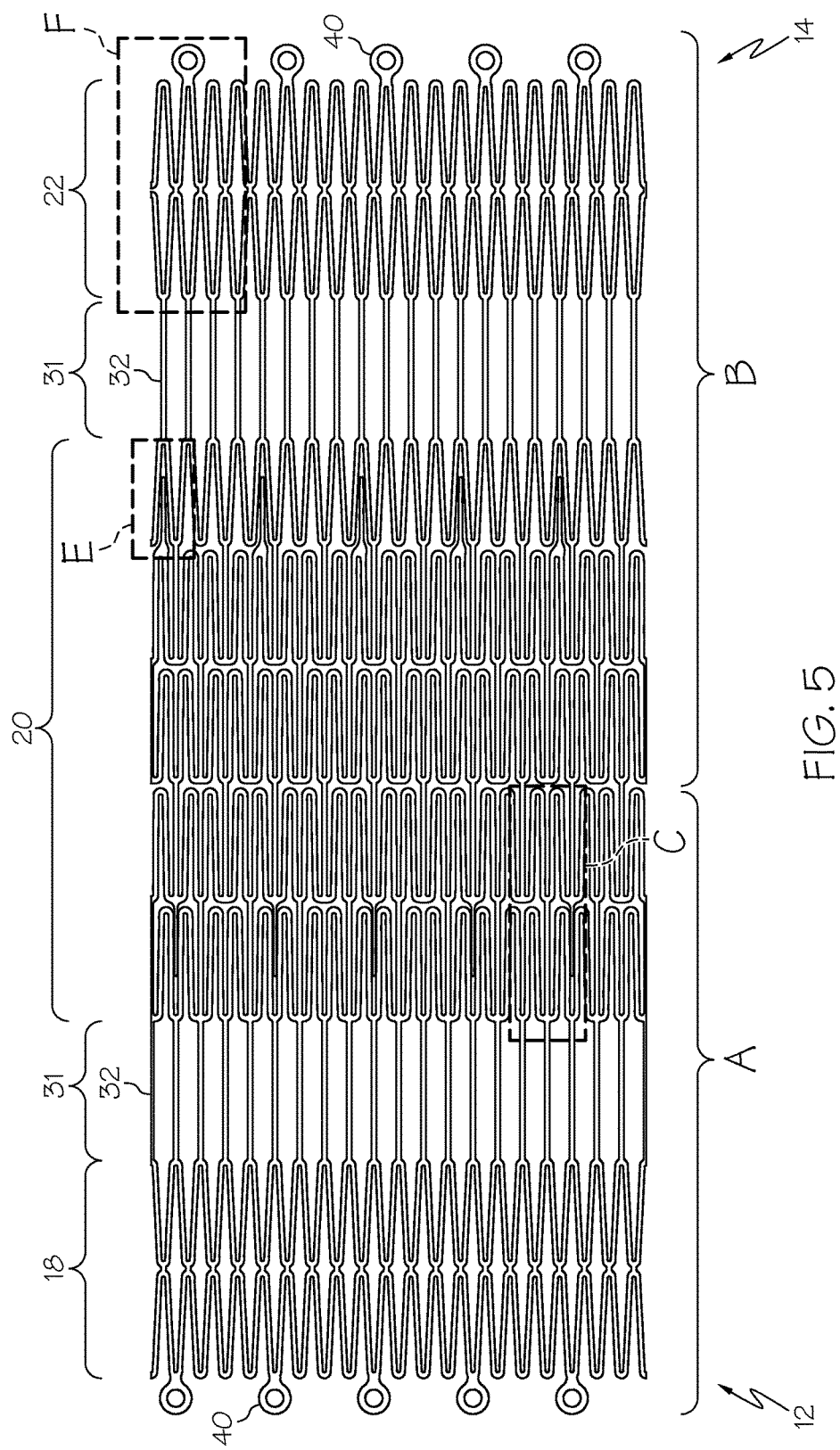
FIG. 5 is a flat plan view of a stent.
Figure 5A:
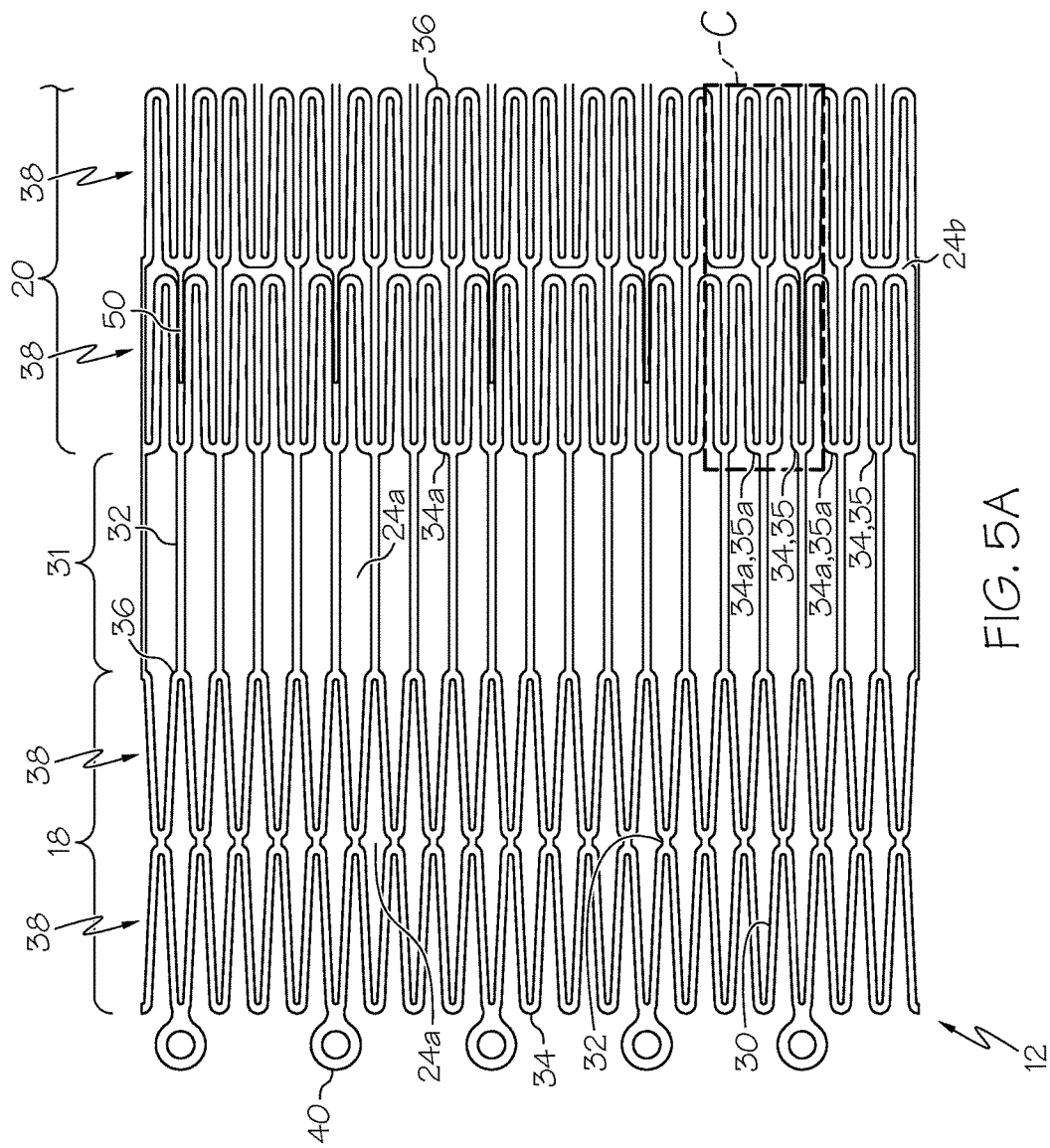
FIG. 5A is an enlarged view of the first part of the stent in FIG. 5.
Figure 5B:
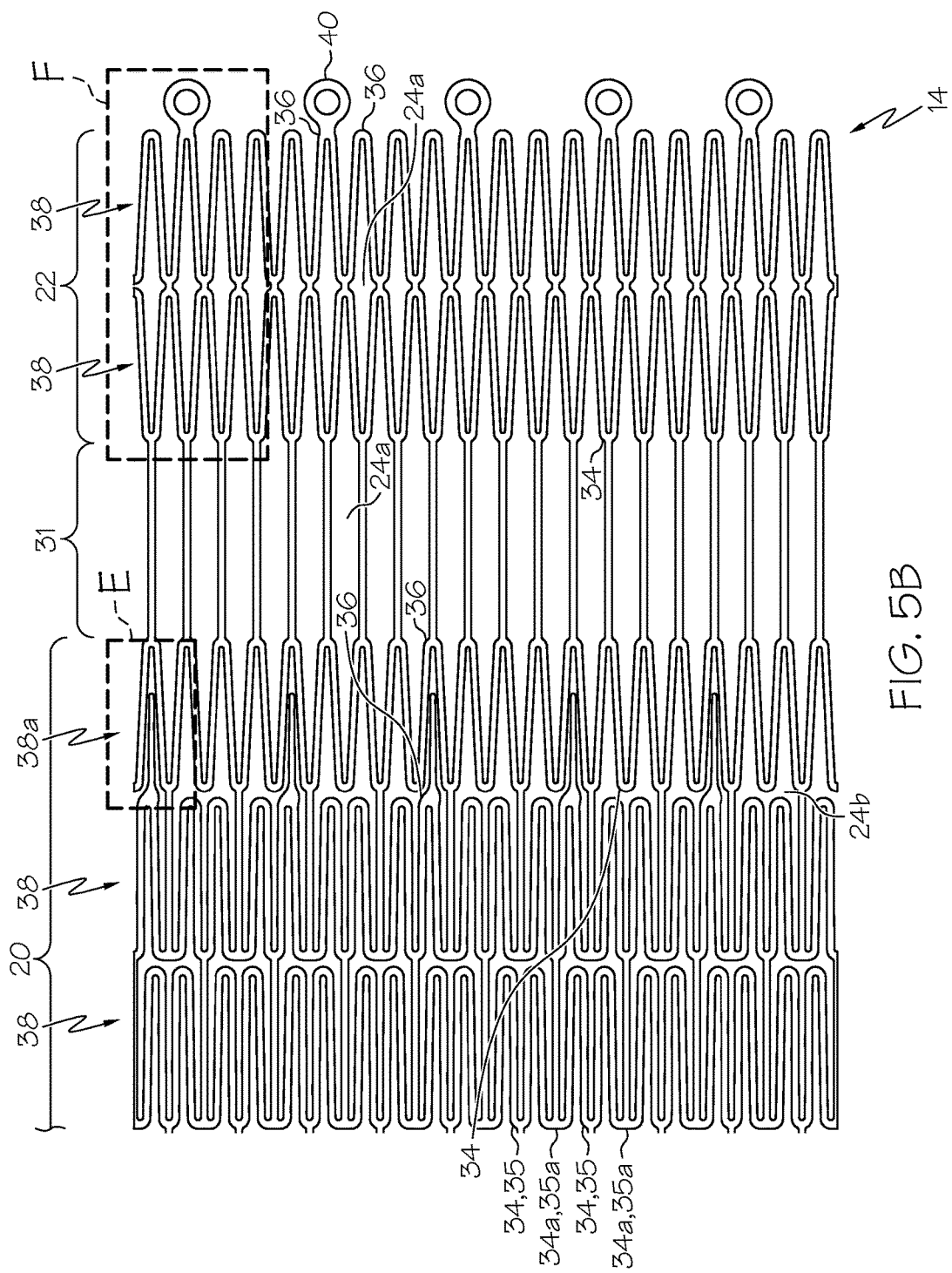
FIG. 5B is an enlarged view of the second part of the stent in FIG. 5.
Figure 5C:
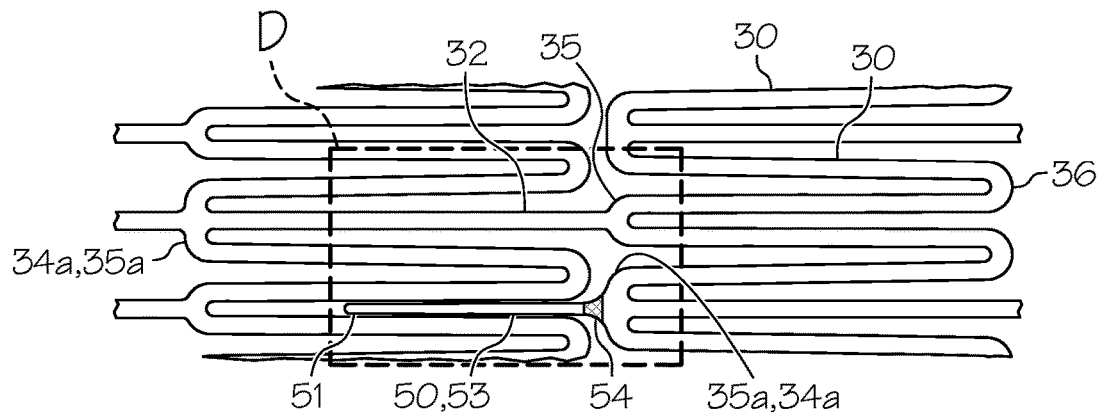
FIG. 5C is an enlarged portion of the stent in FIG. 5.
Figure 5D:
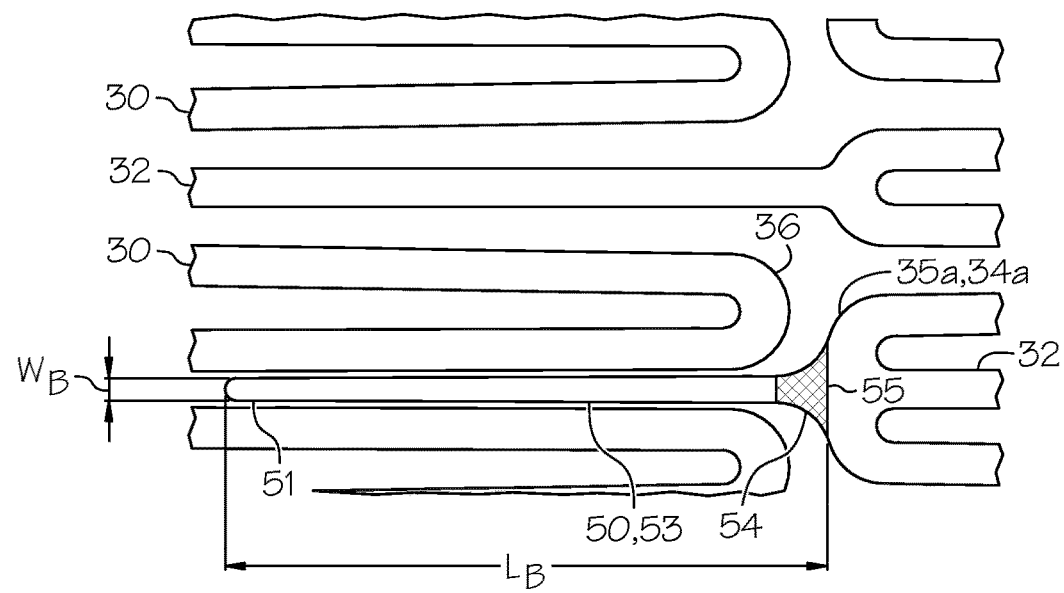
FIG. 5D is an enlarged portion of FIG. 5C.

In some embodiments, the body 53 of the barb 50 has a width that is approximately the same along the length of the body 53. The barbs 50 shown in FIG. 2 have an approximately the same width along the length of the barb 50 until the tip region (indicated by cross-hatching). In other embodiments, the barbs 50 have an approximately the same width from the tip 51 until the end region 54 of the barb 50 which has a greater width than the rest of the barb 50, as shown for example in FIG. 5D-E. In some embodiments, the end region 54 extends from the turn 35 and flares outward relative to the body of the barb 50, as shown for example in FIG. 5D. As shown in FIG. 5D, the end region 54 of the barb 50 gradually increases in width to a maximum width at the turn 35 from which the barb 50 extends.

Figure 7:
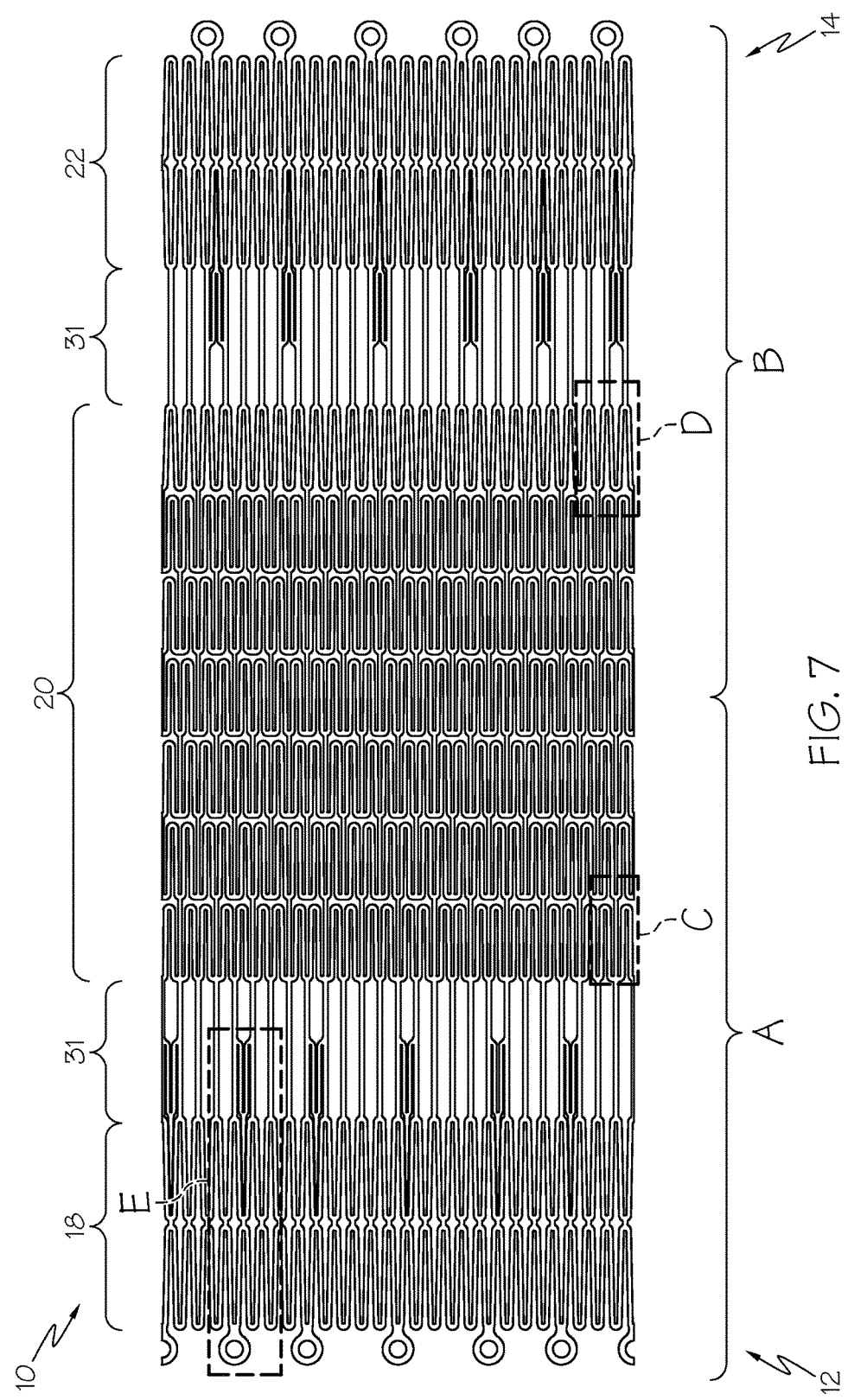
FIG. 7 is a flat plan view of a stent.
Figure 7B:
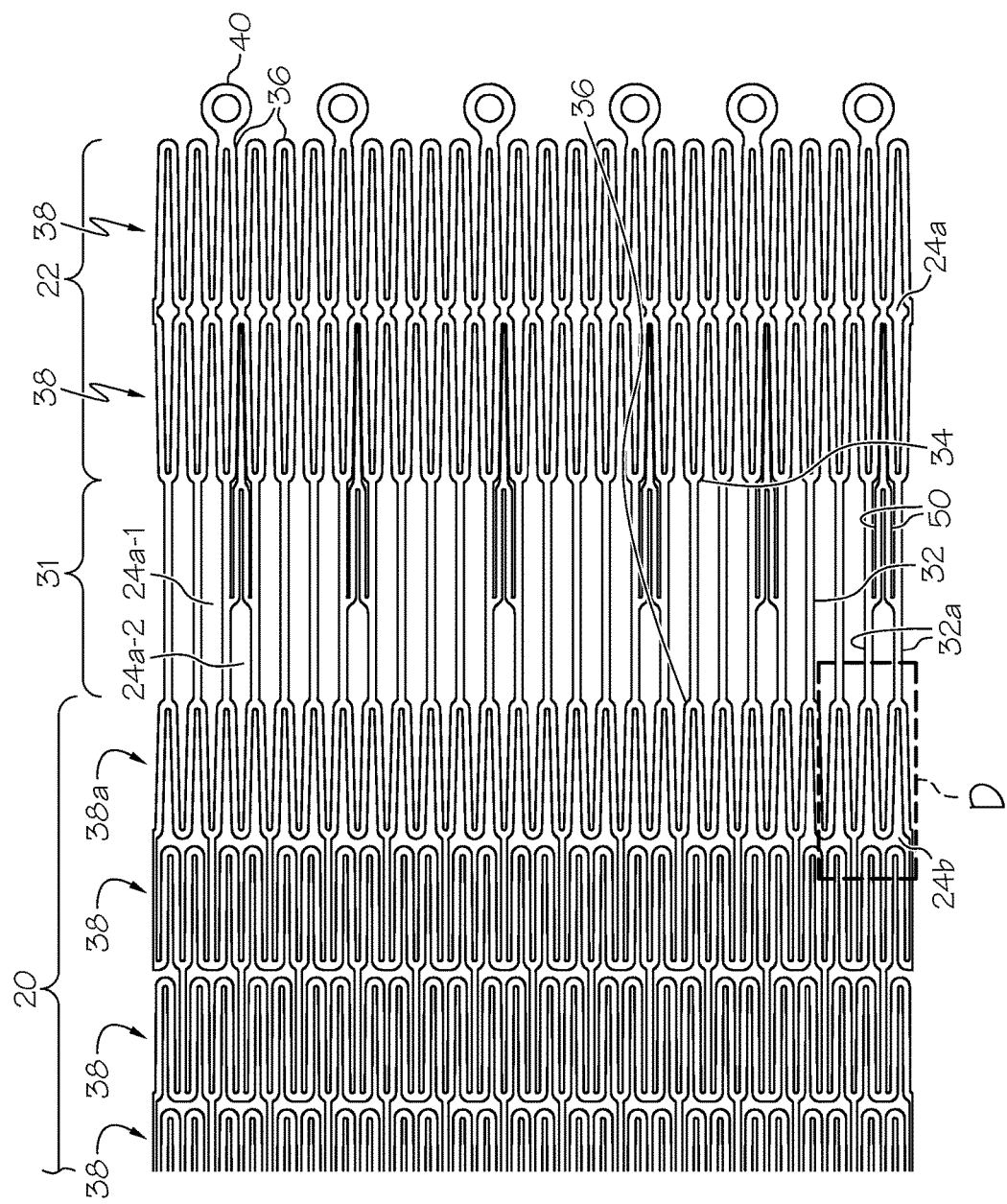
FIG. 7B is an enlarged view of the second part of the stent in FIG. 7.
Figure 7C:
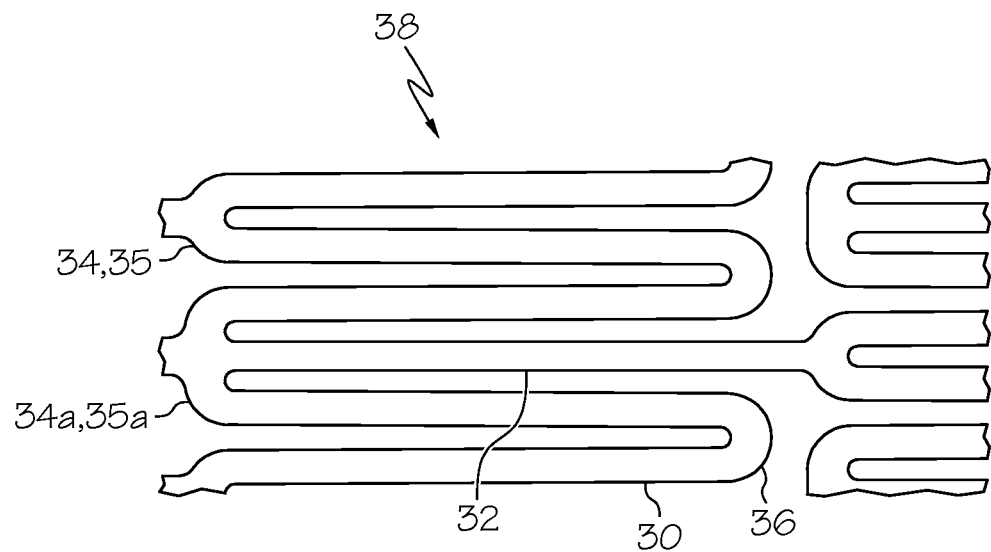
FIG. 7C is an enlarged portion of the stent in FIG. 7.
Figure 7D:
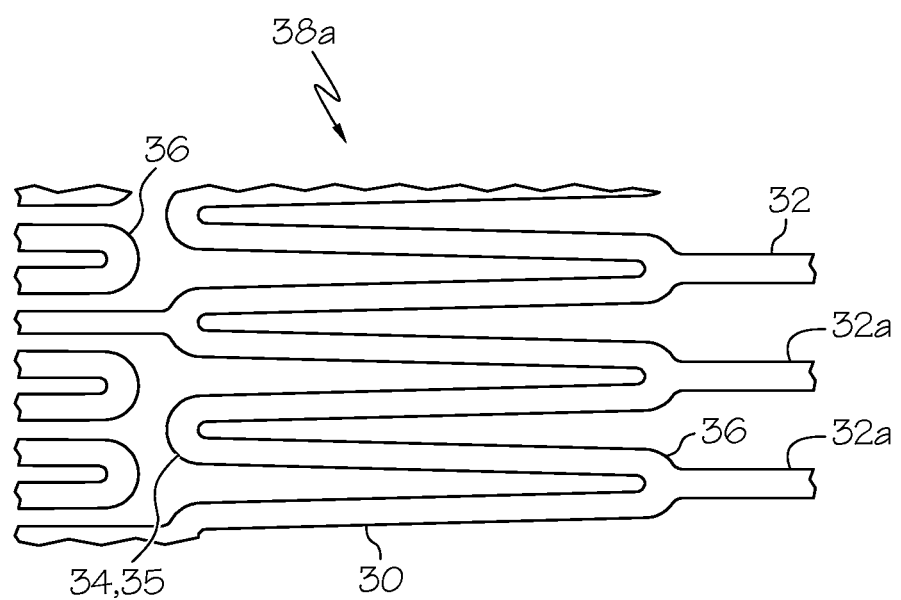
FIG. 7D is an enlarged portion of the stent in FIG. 7.
Figure 7E:
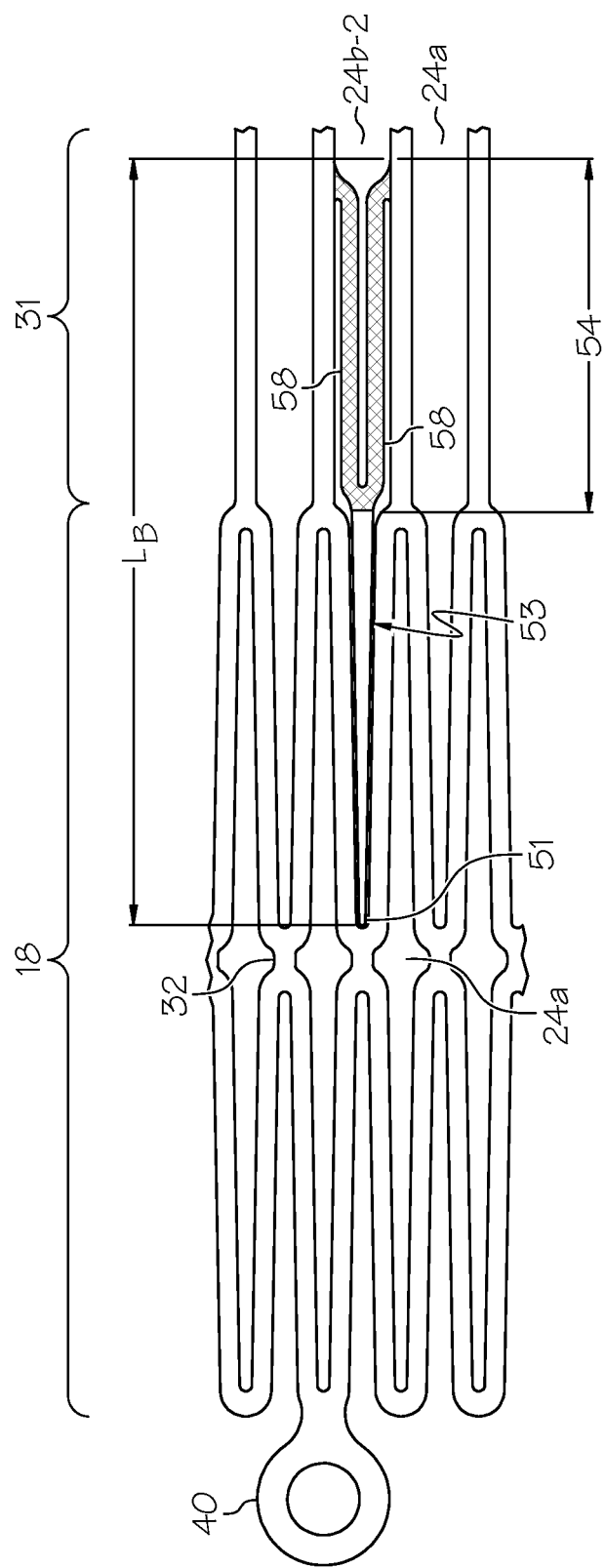
FIG. 7E is an enlarged portion of the stent in FIG. 7.
Figure 8:
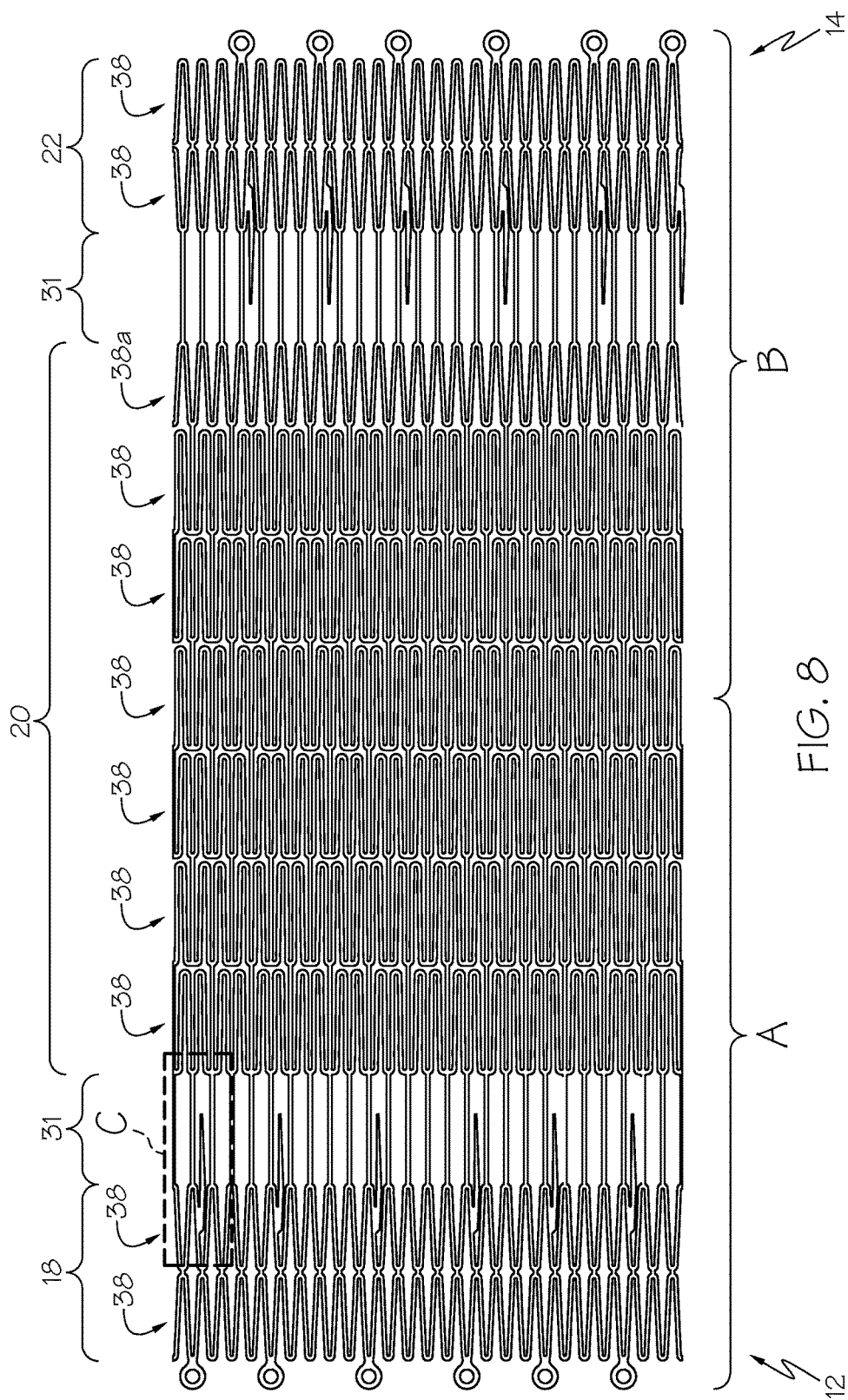
FIG. 8 is a flat plan view of a stent.
Figure 8A:
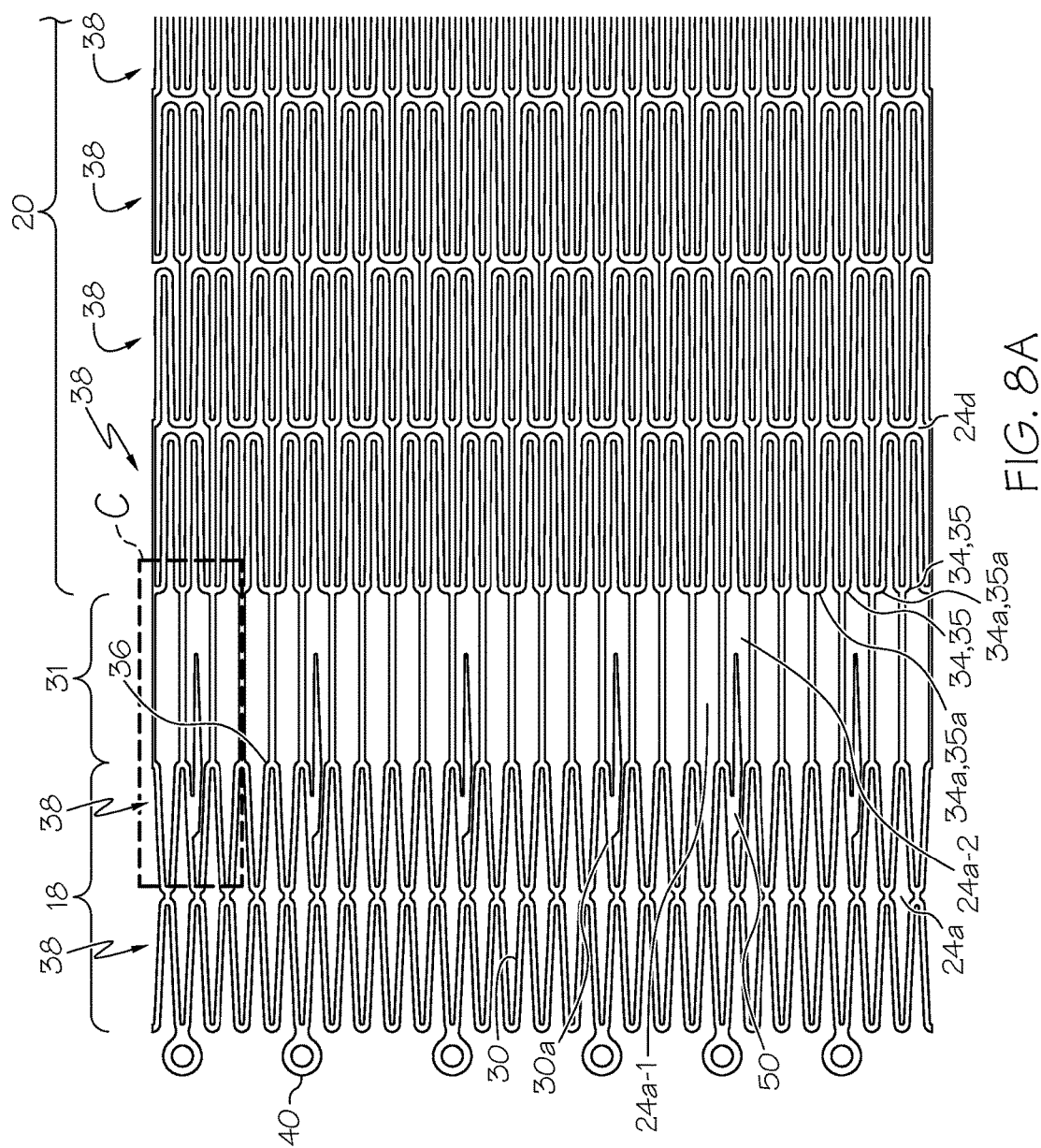
FIG. 8A is an enlarged view of the first part of the stent in FIG. 8.
Figure 8C:
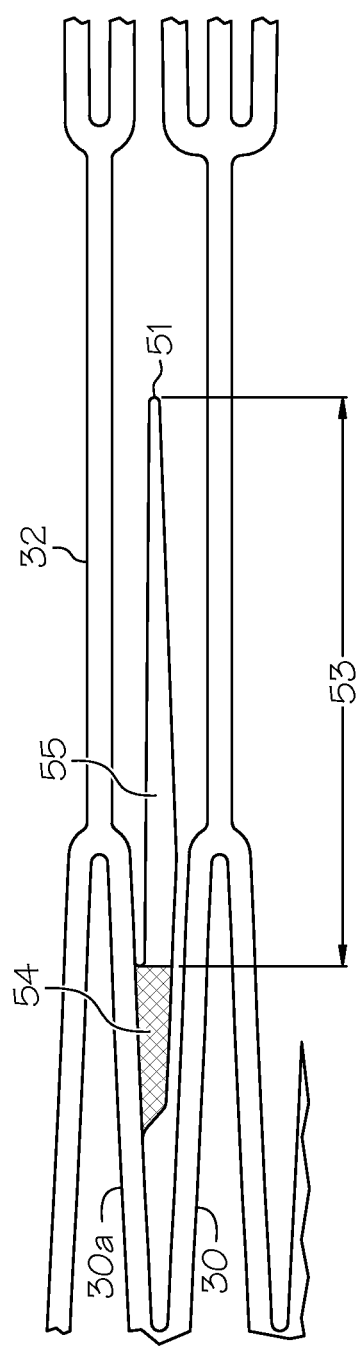
FIG. 8C is an enlarged portion of the stent in FIG. 8
Figure 9:
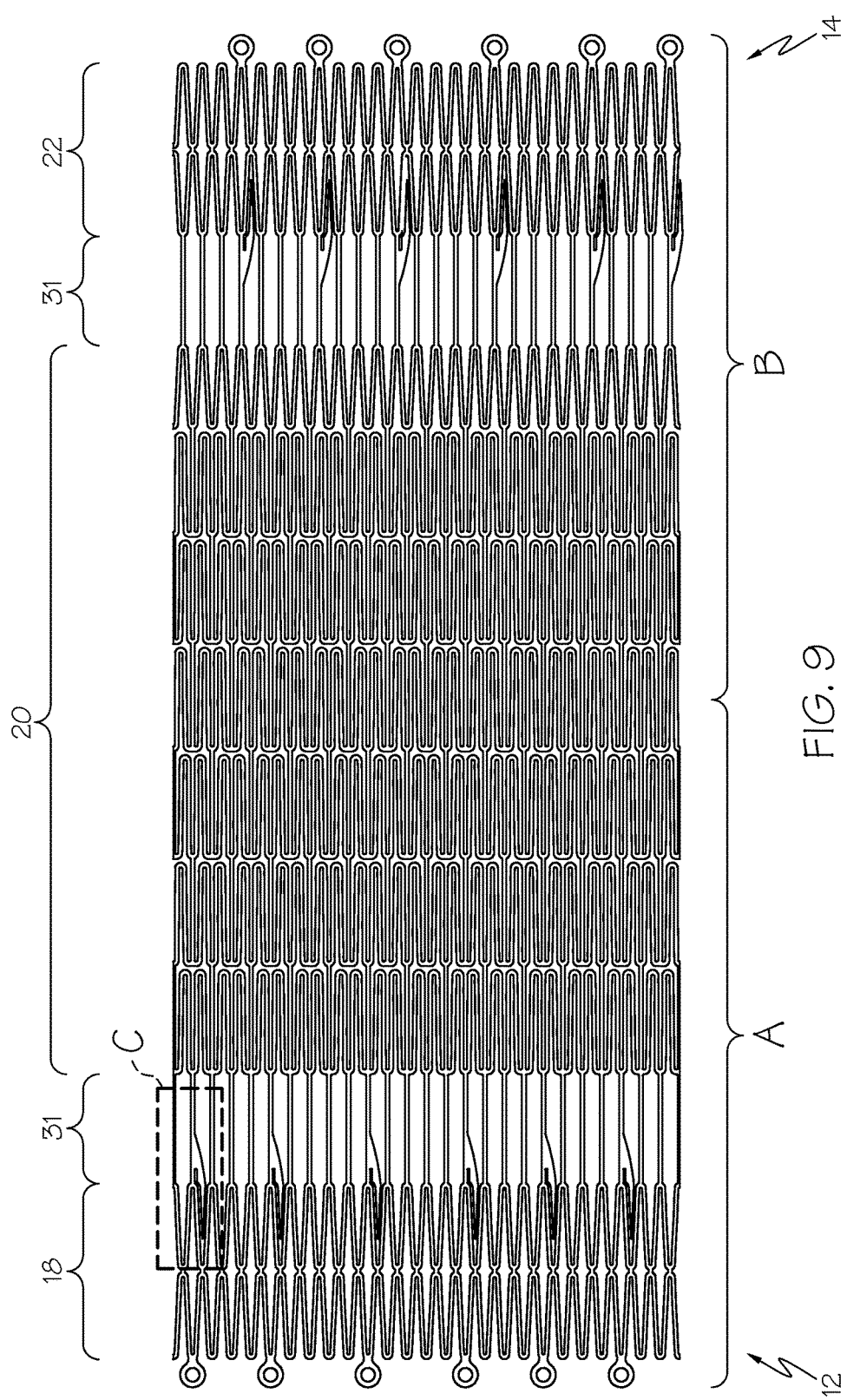
FIG. 9 is a flat plan view of a stent.
Figure 9A:
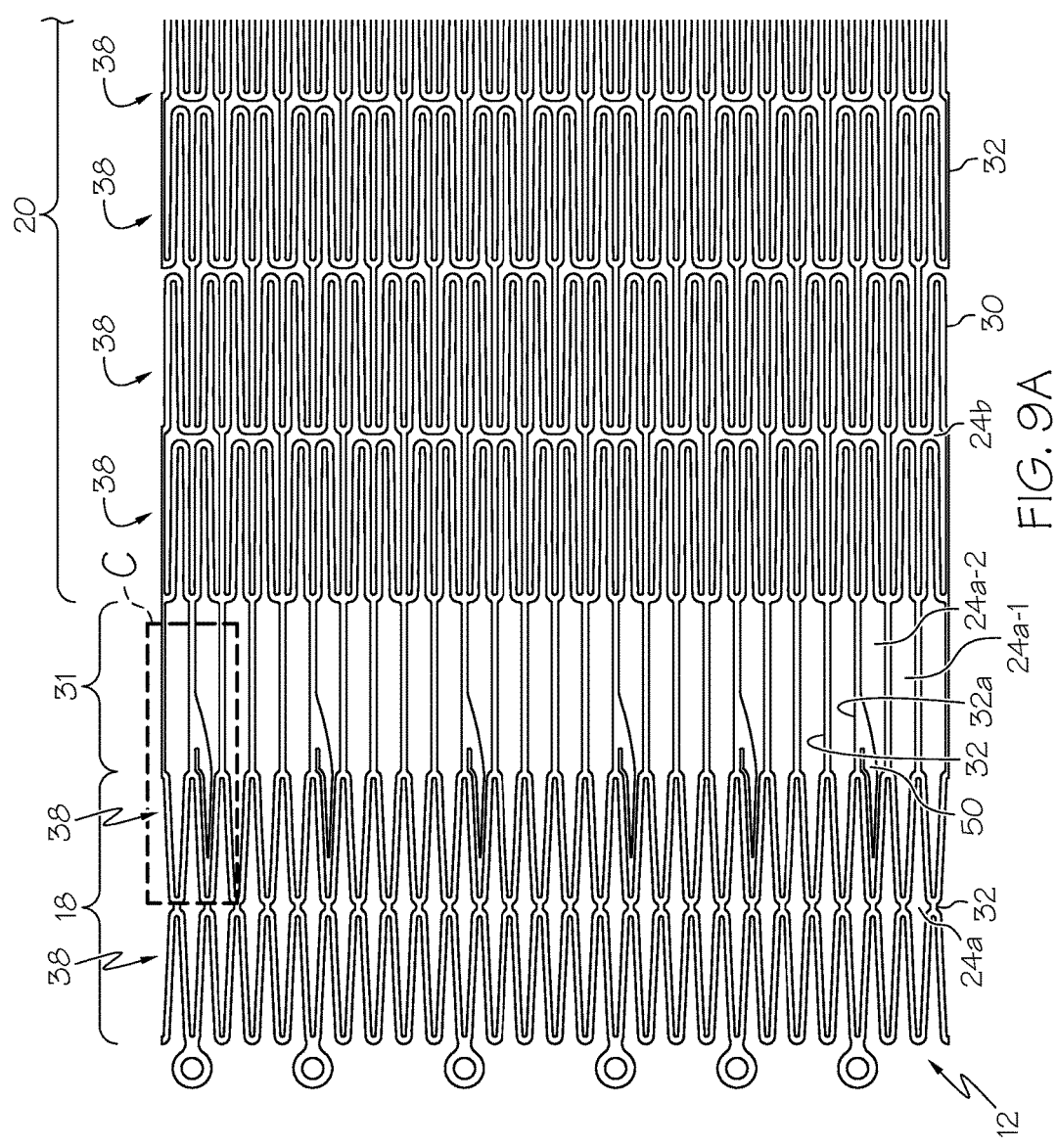
FIG. 9A is an enlarged view of the first part of the stent in FIG. 9.
Figure 9B:
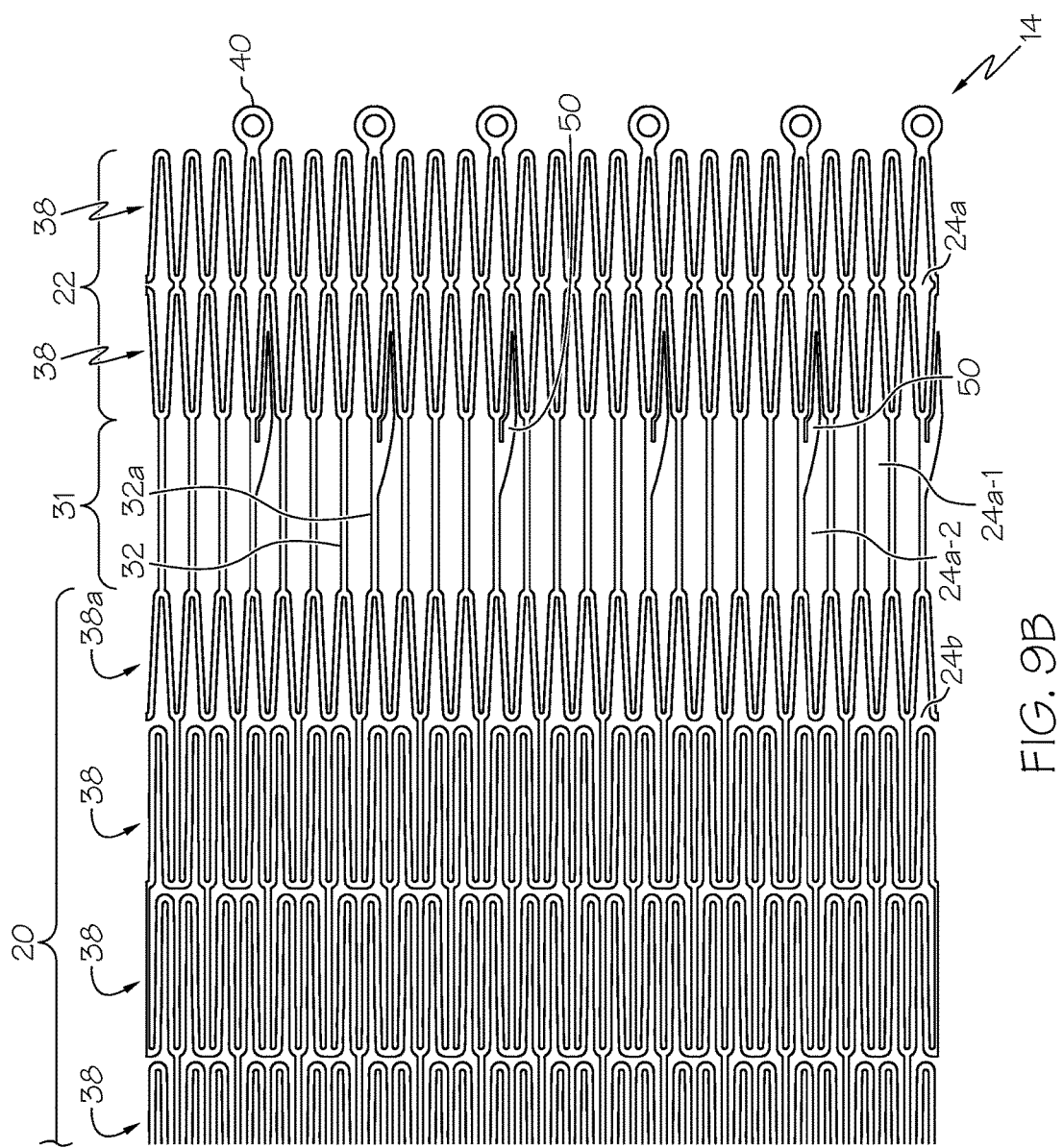
FIG. 9B is an enlarged view of the second part of the stent in FIG. 9.

In at least one embodiment, the body 53 has a variable width. Examples of a barb 50 with a body 53 with a variable width are shown in FIGS. 7-9. In some embodiments the body 53 tapers from the end region 54 to the tip 51. An example of a barb 50 with a tapered body 53 is shown in FIG. 7E. The body 53 of the barb 50 shown in FIG. 8C can be described as comprising two tapered regions with the taper increasing from the end region 54 and increasing from the tip 51 to a maximum width. The barb 50 in FIG. 9C has a tip 51 that has a smaller width than the width of the barb at the junction of the body 53 to the end region 54 and the body 53 has a plurality of widths.

In other embodiments, the end region 54 has a variable width. For example, the end regions 54 of the barbs 50 shown in FIGS. 5E and 6D-E (indicated generally by cross-hatching) extend outwardly relative to the body 53 which is approximately the same width from the tip region until the end region 54.

Figure 5E:
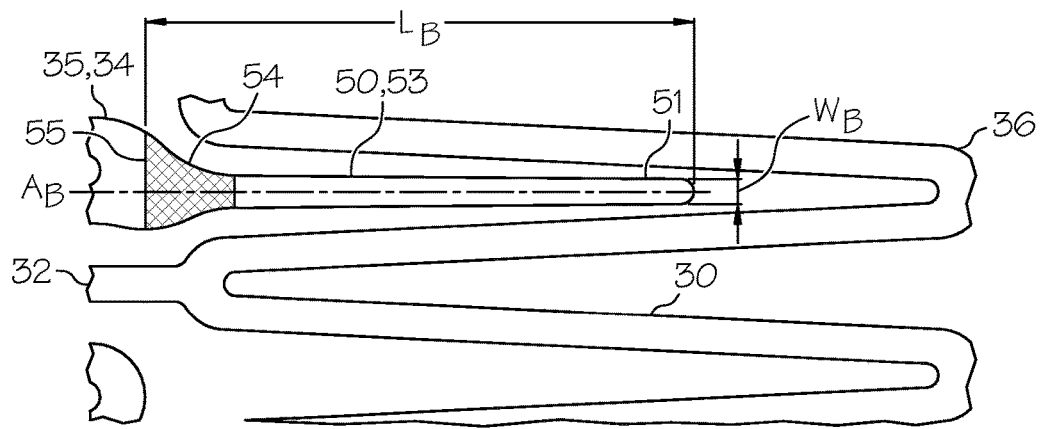
FIG. 5E is an enlarged portion of the stent in FIG. 5.
Figure 5F:
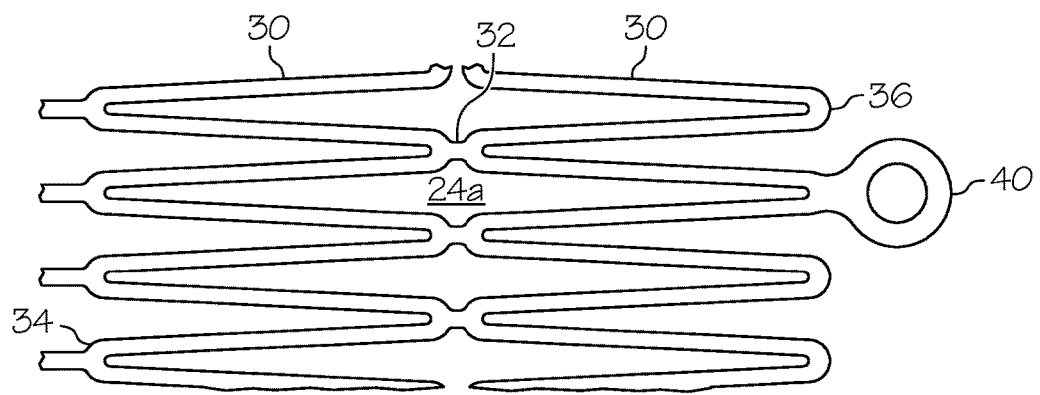
FIG. 5F is an enlarged portion of the stent in FIG. 5.

In at least one embodiment, the tip of the barb is circumferentially offset from the point from which the barb extends from a stent element. For example the barb 50 shown in FIGS. 5E and 6D-E has a tip 51 that is circumferentially offset from the turn 35 from which the barb 50 extends. For example, as shown in FIG. 5E, the tip 51 is circumferentially offset from the turn 35, 34, as shown by axis $A_B$. In at least one embodiment, the amount of offset is the same for each barb 50 of a given strut column 38. In at least one embodiment, the barbs 50 extending from one strut column 38 and the barbs 50 extending from another strut column 38 have the same amount of offset but the offsets are oriented in opposite circumferential directions. This can be seen for example in the stent 10 shown in FIG. 6. In some embodiments, the outwardly extending end region 54 of the barb 50 is constructed to position the barb 50 between two struts 30 of the strut column 38 adjacent to the strut column 38 from which the barb 50 extends, as shown for example in FIGS. 5-6.

In at least one embodiment, the barbs 50 nest between two circumferentially adjacent struts 30 of a strut column. Nesting barbs 50 are shown for example in FIGS. 2-3 and 5-9. In some embodiments, the tip 51 and at least a portion of the body 53 of the barb 50 is positioned between two adjacent struts 30. This can be seen for example in FIGS. 2-3, 5-7, and 9. In other embodiments, the end region 54 and a portion of the body 53 is positioned between two adjacent struts 30. This can be seen for example in FIG. 8.

In some embodiments, the end region 54 of the barb 50 has two legs 58. FIG. 7E shows a non-limiting example of a barb 50 with an end region 54 that has two legs 58. In this embodiment, the legs 58 are engaged to two circumferentially adjacent connectors 32a. Each leg 58 can be described as extending parallel to the connector 32a to which it is connected and as extending parallel to the other leg 58.

Figure 15:
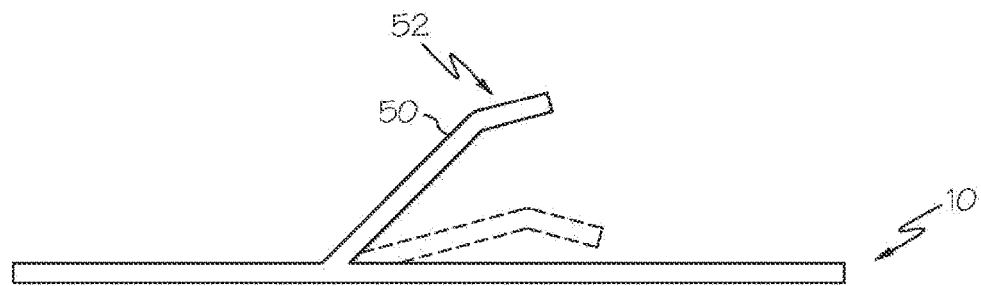

In some embodiments, a portion of the tip region 52 including the tip 51 of the barb 50 is angled relative to the rest of the barb 50, as shown for example in FIG. 15. In FIG. 15, the barb is partially lowered from its expanded position to illustrate its position inside for instance a delivery device.

In one embodiment, the tip of the barb in this partially lowered position does not scrape the inside of a delivery device. In one embodiment, a barb 50 with a tip region 52 that is angled relative to the rest of the barb 50 does not scrape the deliver device as the stent 10 is being delivered to a desired location in a body lumen.

Figure 17:
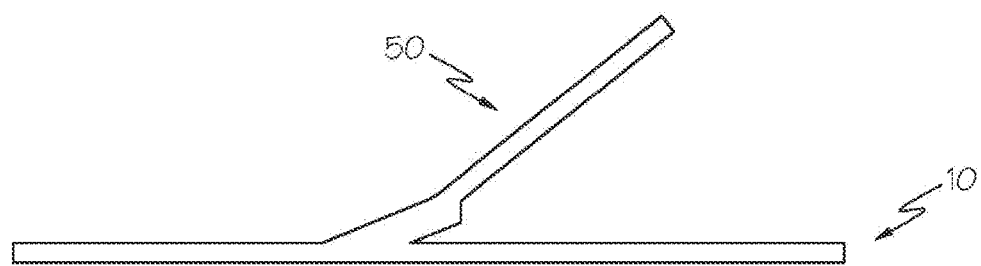

In at least one embodiment, the barb 50 is twisted while it is expanded and heat treated during the manufacturing steps discussed below. FIG. 17 is a schematic view of a barb 50 in an expanded configuration that was twisted during expansion. The twisting helps bending the barb when the barb width is smaller than the wall thickness.

In at least one embodiment, the tip 51 of the barb 50 in an expanded state prevents migration of the stent 10 after the stent 10 has been deployed in a body lumen. In at least one embodiment, the barb 50 in an expanded state is at an angle to the outer surface of the stent 10. The barb 50 in the expanded state can also be described as being at an angle to the longitudinal axis of the stent 10. In some embodiments, the angle of the barb 50 relative to the outer surface of the stent 10 is about 30° to about 60°. In one embodiment, the angle of the barb 50 in the expanded state relative to the outer surface of the stent 10 is 45°. This is shown for example in FIG. 13. In at least one embodiment, the angle of the barbs relative to the outer surface of the flared portion of the stent is the same as the angle of the barbs relative to the outer surface of the non-flared portion of the stent.

Figure 16:
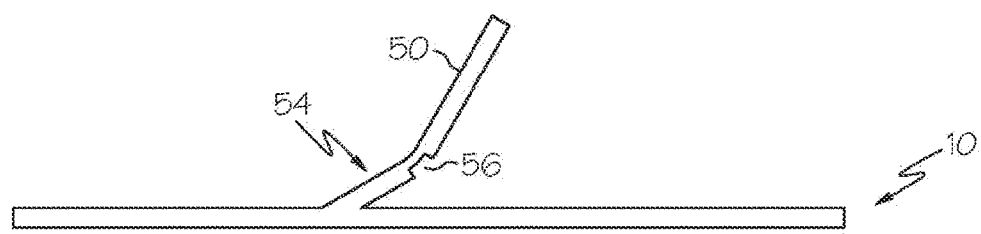

In other embodiments, the barb 50 has a modification at or near the end region 54 that modifies the angle of the barb 50 relative to the outer surface of the stent 10 when the barb 50 is in an expanded state. In one embodiment, the modification to the barb 50 at or near the end region 54 is a focal removal 56 of barb material. FIG. 16 is a non-limiting example of a barb 50 with a focal removal 56. As shown in FIG. 16, some of the barb material is removed from an inner surface of the barb 50. It is within the scope of the invention for the focal removal to be in the form of a spot or to have any length and width. In some embodiments, the barb 50 has a smaller thickness at the focal removal 56 than at the rest of the barb 50. Thus a barb 50 with a focal removal 56 can be described as having a variable thickness along the length of the barb. In other embodiments, the focal removal 56 extends between both sides of the barb 50. In other words, the focal removal spans the entire width of the barb. In some embodiments, the focal removal has a width less than the width of the barb. In one embodiment, the focal removal is positioned between the two sides of the barb. In other words, the barb material is a cavity defined by the inner surface of the barb. In another embodiment, the focal removal extends from one side of the barb to a position between the two sides of the barb. In some embodiments, the focal removal is tapered at the edges. In at least one embodiment, a barb 50 with a focal removal 56 is positioned at a more acute angle relative to the outer surface of the stent 10 when the barb 50 is in an expanded state.

A2. The Stent

In at least one embodiment, the stent 10 includes a first end 12, a first end region 18, a middle region 20, and a second end region 22, a second end 14, an outer surface, and an inner surface that defines a lumen. Each region 18, 20, 22 of the stent 10 includes at least one strut column 38. Each strut column 38 comprises a plurality of struts 30 interconnected by turns 35 that are either peaks 34 or valleys 36. In at least one embodiment, each strut column 38 has a serpentine configuration.

In at least one embodiment, the first end region 18, the middle region 20, and the second end region 22 have approximately the same diameter when the stent 10 is in the as cut state. In some embodiments, the first and second regions of the stent have approximately the same diameter when the stent is in the parent state. In other embodiments, the first and second end regions have a greater diameter than the middle region when the stent is in the parent state (not shown). In some embodiments, the first and second end regions 18, 22 are flared relative to the middle region 20 when the stent 10 is in the parent state. In one embodiment, the first end region has a gradually decreasing outer diameter from first end of the stent/first end of the first end region to the second end of the first end region, and the second end region has a gradually decreasing outer diameter from the second end of the stent/second end of the second end region to the first end of the second end region. In other embodiments, the first and second end regions have a first diameter and the middle diameter has a second diameter where the second diameter is less than the first diameter and each diameter is approximately the same along the length of the region. Thus the structural relationship of the regions 18, 20, 22 of the stent 10 is different when the stent 10 is in the as cut state than when the stent 10 is in the parent state. In at least one embodiment, the first and second end regions each have a diameter of 21 mm and the middle region has a diameter of 18 mm when the stent is in the parent state.

In at least one embodiment, the stent 10 includes a plurality of connectors 32 extending between adjacent strut columns 38. In some embodiments, the end regions 18, 22 of the stent have connectors 32 extending between turns facing in opposite directions, e.g. peak to valley connectors; the middle region 20 has connectors 32 extending between turns facing in the same direction, e.g. peak to peak connectors or valley to valley connectors; and the connectors extending between the middle region 20 and the end regions 18, 22 extend between turns facing opposite directions, e.g. peak to peak connectors or valley to valley connectors. This is shown for example in FIGS. 2 and 5-9.

In at least one embodiment, each end region 18, 22 has at least one strut column 38. As shown in the figures, each end region 18, 22 has two strut columns 38. However, it is within the scope of the invention for the end regions 18, 22 to have at least one strut column 38. In at least one embodiment, each strut column 38 in the end regions 18, 22 has a plurality of strut pairs, or a plurality of struts. In one embodiment, each strut column 38 in the end regions 18, 22 has twenty (20) struts pairs or forty (40) struts. In another embodiment, each strut column 38 in the end regions 18, 22 has twenty-six (26) strut pairs or fifty-two (52) struts. However, the strut column can have any desired number of struts. In at least one embodiment, the strut columns 38 of the end regions 18, 22 have narrow turns.

In some embodiments, the two strut columns 38 forming an end region 18, 22 are out of phase and a plurality of peak to valley connectors 32 extend between longitudinally adjacent strut columns 38. In some embodiments, the peak to valley connectors 32 extending between the strut columns 38 of an end region 18, 22 are very short connectors 32. In one embodiment, the very short connectors 32 have a first length and the connectors 32 forming the connector regions 31 have a second length where the first length is less than the second length.

As shown in FIGS. 2 and 5-9 the connectors 32 extend between every peak 34 and valley 36 of the adjacent strut columns 38 forming the end region 18, 22. As can be seen in the enlarged portion of an end region 18, 22 of the stent 10, the end region has two strut columns 38 that define a plurality of closed cells 24a. In some embodiments, the cells defined by adjacent strut columns 38 in an end region 18, 22 each have the same shape. In one embodiment, the end regions 18, 22 define a plurality of closed cells that are diamond shaped. In some embodiments, the closed cells 24a in the end regions 18, 22 have a different configuration or shape than the closed cells 24a between an end region 18, 22 and the middle region 20. This can be seen for example in FIG. 2. In other embodiments, the closed cells 24a in the end regions 18, 22 are smaller than the closed cells between an end region 18, 22 and the middle region 20.

In at least one embodiment, some of the plurality of connectors 32 form two connector regions 31 with one connector region 31 extending between the first end region 18 and the middle region 20 and the other connector region 31 extending between the middle region 20 and the second end region 22. In some embodiments, each connector region 31 has twenty (20) connectors 32. In other embodiments, each connector region 31 has twenty-six (26) connectors 32. In one embodiment, the connectors 32 in the connector regions 31 are approximately straight and have the same length. In at least one embodiment, the connectors 32 in the connector regions 31 have a width of about 0.007 inches (0.178 mm).

In some embodiments, when the stent 10 is in the parent state the connectors 32 extending between the middle region 20 and the first end region 18 are at an angle relative to the outer surface of the middle region 20 of the stent 10 and the connectors 32 extending between the middle region 20 and the second end region 22 are at an angle relative to the outer surface of the middle region 20 of the stent 10.

In some embodiments, as shown in FIGS. 2 and 5-9, the connectors 32 extending between an end region 18, 22 and the middle region 20 are peak to valley connectors 32 and extend between every peak 34 on one strut column 38 and every valley 36 of the other strut column 38. In this embodiment, the stent 10 has a plurality of closed cells 24a between the first end region 18 and the middle region 20 and a plurality of closed cells 24a between the middle region 20 and the second end region 22.

In some embodiments, the closed cells 24a between an end region 18, 22 and the middle region 20 each have the same shape when the stent is in the as-cut state and when the stent is in the parent state. In other embodiments, the closed cells 24a between the first end region 18 and the middle region 20 have a different shape than the closed cells 24a between the middle region 20 and the second end region 22. This can be seen for example in FIG. 5 where the configuration of the first strut column 38 of the middle region is different from the configuration of the last strut column 38a of the middle region, which affects the shape of the closed cells 24a between the first end region 18 and the middle region as compared to the shape of the closed cells 24a between the middle region and the second end region 22.

In other embodiments, the closed cells 24a between an end region 18, 22 and the middle region are different shapes. For example, in FIG. 7, between the first end region 18 and the middle region 20 are first closed cells $24a_1$ having a first shape and second closed cells $24a_2$ having a second shape different than the first shape when the stent is in the as-cut state. In some embodiments, the different shapes of the closed cells 24a between an end region 18, 22 and the middle region 20 is due to a barb 50 positioned within the closed cell 24a when the stent is in the as-cut state. This can be seen for example in FIG. 7, where closed cells $24a_{1,2}$ where a barb 50 positioned within the second closed cell $24a_2$. Similarly, as shown in FIG. 8, the shapes of the first closed cells $24a_1$ and the second closed cells $24a_2$ between the first end region 18 and the middle region 20 are different with a barb 50 being positioned within the second closed cells 24$a_2$ when the stent is in the as-cut state.

In other embodiments, the connectors are peak to valley connectors and extend between fewer than all the peaks (not shown). In this embodiment, the stent has a plurality of open cells between the first end region and the middle region and a plurality of open cells between the middle region and the second end region.

In some embodiments, the stent 10, the delivery system or other portion of the assembly may include one or more areas, bands, coatings, layers, members, etc. that is (are) detectable by imaging modalities such as X-Ray, MRI, ultrasound, etc. In some embodiments, at least a portion of the stent 10 and/or adjacent assembly is at least partially radiopaque.

In some embodiments, the stent 10 has a plurality of integrally formed paddles 40 designed to receive a radiopaque marker made out of tantalum or any other element or alloy with high atomic number. As shown in the figures, the paddles 40 have a circular shape. However, the paddles 40 can have any suitable configuration. In at least one embodiment, the stent 10 has a plurality of paddles 40 attached to the first and second ends 12, 14 of the stent. In some embodiments, the stent 10 has five (5) paddles 40 extending from the peaks of the strut column 38 at the first end 12 of the stent and five (5) paddles 40 extending from the valleys 36 of the strut column 38 at the second end 14 of the stent. In other embodiments, the stent 10 has six (6) paddles 40 extending from the peaks of the strut column 38 at the first end 12 of the stent and six (6) paddles 40 extending from the valleys of the strut column at the second end 14 of the stent. In at least one embodiment, the paddles extend from some, but not all, of the peaks 34 of the first end 12 of the stent and some, but not all, of the valleys 36 of the second end 14 of the stent 10. In some embodiments, the paddles 40 extend from every fourth turn 35. In other embodiments, the paddles 40 extend from every fifth turn 35.

In at least one embodiment, the middle region 20 has a plurality of strut columns 38 comprising a plurality of turns 35 interconnecting a plurality of struts 30. FIGS. 2-3 and 5-9 provide non-limiting examples of patterns for the strut columns 38 in the middle region 20. In some embodiments, the strut columns 38 in the middle region 20 each have twenty (20) strut pairs or forty (40) struts 30. In other embodiments, the strut columns 38 in the middle region 20 each have twenty-six (26) strut pairs or fifty-two (52) struts.

In at least one embodiment, the middle region 20 comprises a plurality of connectors 32. In some embodiments, ten (10) connectors 32 extend between adjacent strut columns 38. In other embodiments, thirteen (13) connectors 32 extend between adjacent strut columns 38. In one embodiment, the connectors 32 in the middle region 20 are peak to peak connectors 32. In some embodiments, the connectors 32 are approximately straight and parallel to the longitudinal axis of the stent, as shown for example in FIG. 2A. In one embodiment, the connectors 32 in the middle region 20 are shorter than the connectors 32 in the connector regions 31 and longer than the connectors 32 in the end regions 18, 22. In at least one embodiment, the middle region 20 defines a plurality of open cells 24b, as shown for example in FIG. 2C.

In some embodiments, the strut columns 38 forming the middle region 20 have the same configuration (not shown). In at least one embodiment, one strut column 38a forming an end of the middle region 20 has a different configuration than the other strut columns 38. This is shown for example in FIGS. 2 and 5-9. In some embodiments, the strut column 38a does not have any chevron turns 35a. In one embodiment the strut column 38a in the middle region 20 has the same configuration as the strut columns forming the end region 22 of the stent 10 to which the strut column 38a is connected. This can be seen for example in FIGS. 2 and 5-9. In some embodiments, the turns 35 of adjacent strut columns 38 in the middle region 20 are circumferentially offset from one another. This can be seen for example in FIG. 6C.

In at least one embodiment, the middle region 20 includes a plurality of chevron turns 35a. In at least one embodiment, the chevron turns 35a are directed to the same end of the stent 10. For example, as can be seen in FIGS. 2 and 5-9 the chevron turns 35a all are directed towards the first end 12 of the stent 10. In some embodiments, the each chevron turn 35a in the middle region 20 of the stent 10 has a connector 32 connected thereto.

In at least one embodiment, at least some of the strut columns 38 of the middle region 20 of the stent 10 can also be described as comprising a plurality of chevron turns 35a and a plurality of turns 35 forming one end of the strut column 38 and a plurality of turns 35 forming the second end of the strut column 38.

In some embodiments, the turns 35, 35a at the first end of the strut column 38 form a pattern where the chevron turns 35a are in groups of three and each group of three chevron turns 35a are separated from an adjacent group of three chevron turns 35a by a turn 35 (35-35a-35a-35a-35-35a-35a-35a-35 . . . ). This is shown for example in FIG. 2. In other embodiments, the turns 35, 35a at the first end of the strut column 38 are alternating with one another about the circumference of the stent 10 (35a-35-35a-35 . . . ). This is shown for example in FIGS. 5-9.

Alternatively, in at least one embodiment, the middle region 20 can be described as having a plurality of strut columns where one strut column 38a only has narrow peaks and narrow valleys (no wide peaks or valleys), and the other strut columns 38 have wide peaks 34a, narrow peaks 34, and only narrow valleys (no wide valleys). This is shown for example in FIGS. 2 and 5-9. In some embodiments, the wide peaks 34a and narrow peaks 34 of a strut column form a pattern that repeats along the strut column where the pattern is three wide peaks and one narrow peak (e.g. 34-34a-34a-34a-34-34a-34a-34a-34a-34 . . . ). This is shown for example in FIG. 2. In other embodiments, the wide peaks 34a and narrow peaks 34 of a strut column alternate along the strut column (e.g. 34a-34-34a-34 . . . ). This is shown for example in FIGS. 5-9. As can be seen in the figures, the wide peaks 34a have a greater circumferential width than the narrow peaks 34 ($W_1 > W_2$). In at least one embodiment, the narrow valleys 36 having a circumferential width ($W_3$) that is approximately the same as the narrow peaks 34.

In some embodiments, wider turns 34a, 35a are needed to accommodate the peak to peak connectors 32. In at least one embodiment, the wider turns 34a, 35a are larger than the smaller 34, 35 turns by approximately one width of connector 32.

A3. The Stent with Barbs

In at least one embodiment, at least one region 18, 20, 22, 31 of the stent 10 has a plurality of barbs 50. As shown for example in FIG. 2, the middle region 20 of the stent 10 has a plurality of barbs 50. As shown for example in FIG. 8, the end regions 18, 22 of the stent 10 have a plurality of barbs 50. As shown for example in FIGS. 7 and 10, the connector regions 31 have a plurality of barbs 50.

In other embodiments, the tips 51 of the barbs 50 face both ends 12, 14 of the stent 10. For example, the barbs 50 of the stents 10 shown in FIGS. 5 and 7-9 face both ends 12, 14 of the stent 10. As can be seen, the barb 50 shown in FIG. 5D faces the first end 12 while the barb 50 shown in FIG. 5E faces the second end 14.

In some embodiments, the stent 10 has from six (6) to twenty (20) barbs 50. In at least one embodiment, the middle region 20 of the stent 10 has six (6) strut columns 38 with each strut column including a desired number of barbs 50, x, for a total number of barbs 50 y, where y is the total number of barbs 50 for the stent 10 (6x). In other embodiments, the stent 10 has twelve (12) barbs, as shown for example in FIG. 7.

In at least one embodiment, the spacing design of connectors 32 and barbs 50 provide for uniform distribution of stresses, enhanced flexibility, and balanced anchoring within the lumen.

Figure 6:
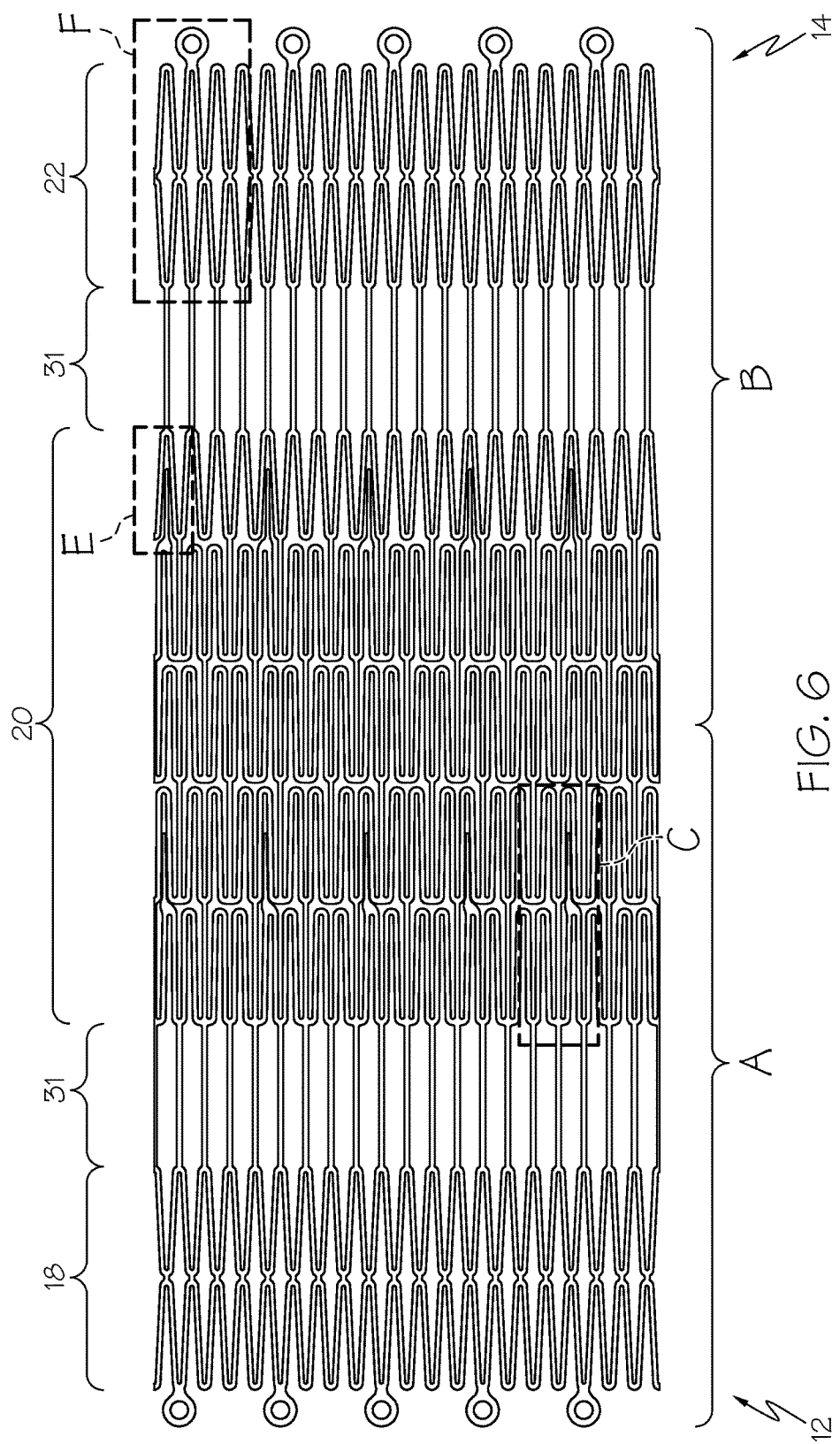
FIG. 6 is a flat plan view of a stent.
Figure 6B:
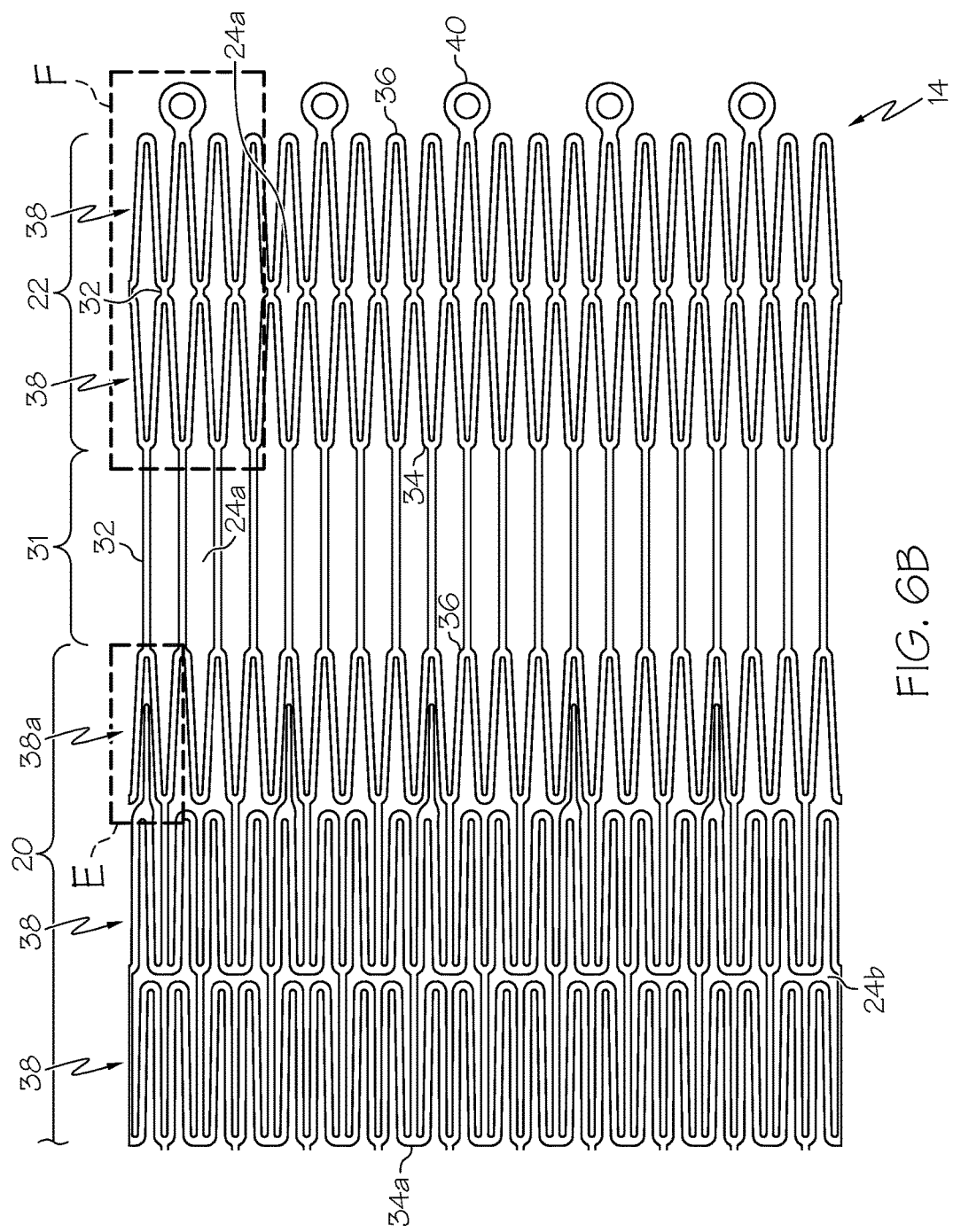
FIG. 6B is an enlarged view of the second part of the stent in FIG. 6.
Figure 6C:
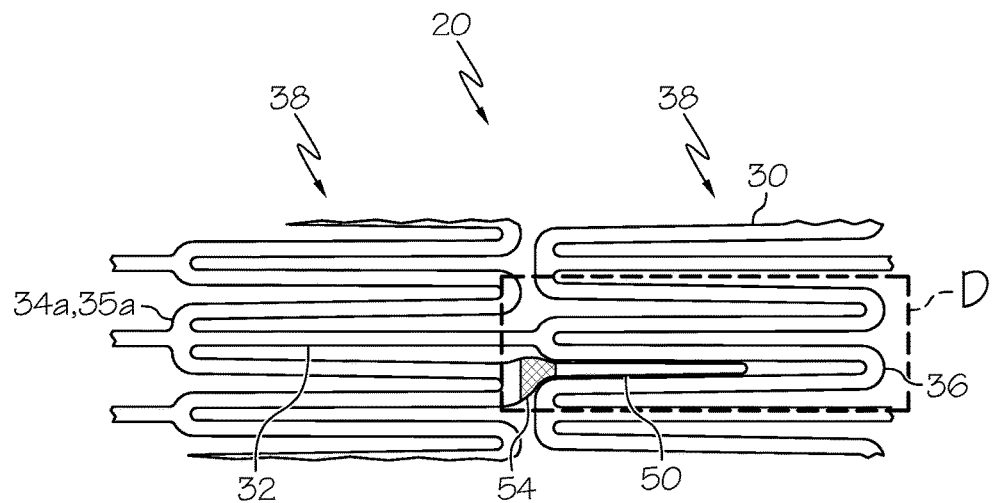
FIG. 6C is an enlarged portion of the stent in FIG. 6.
Figure 6D:
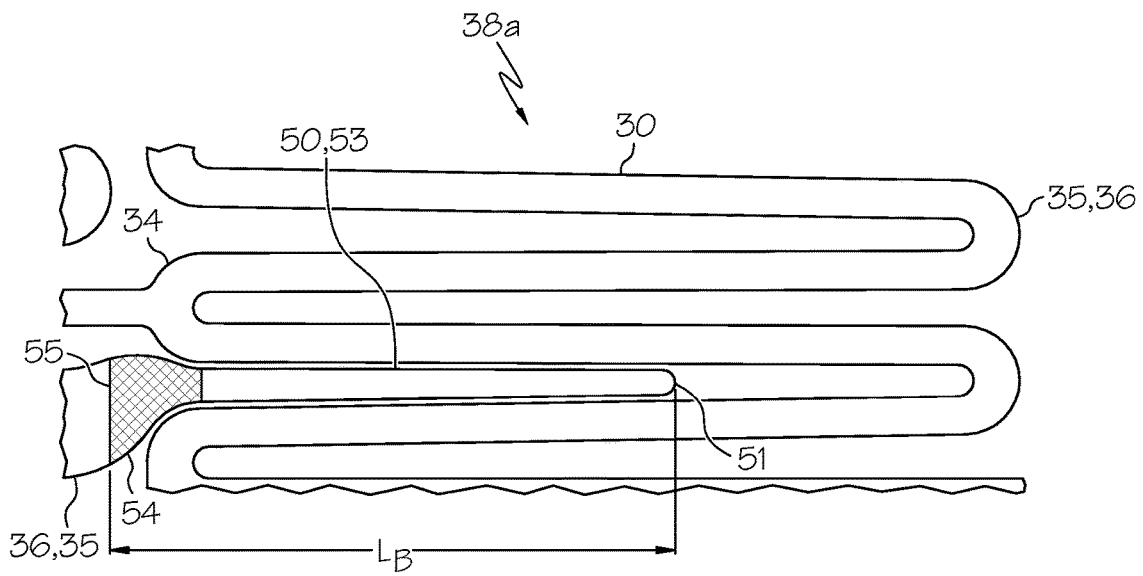
FIG. 6D is an enlarged portion of FIG. 6C.
Figure 6E:
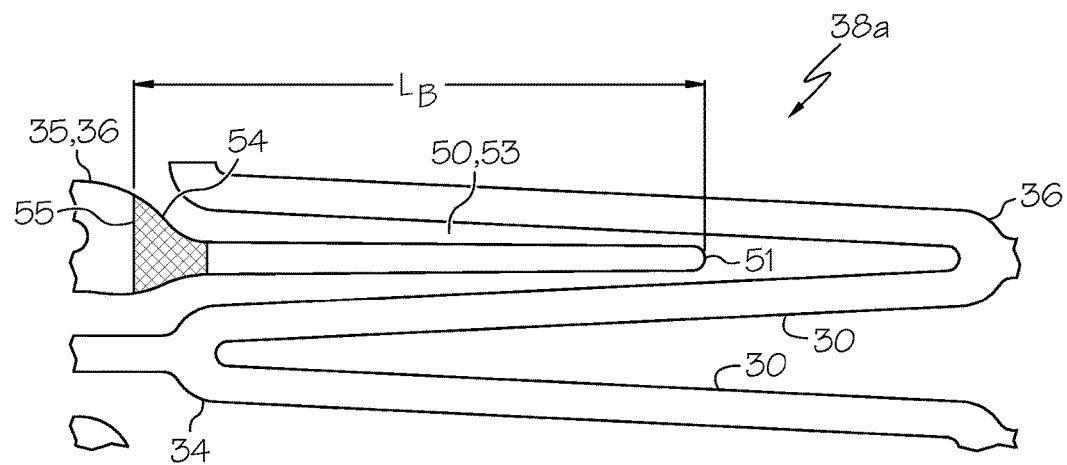
FIG. 6E is an enlarged portion of the stent in FIG. 6.
Figure 6F:
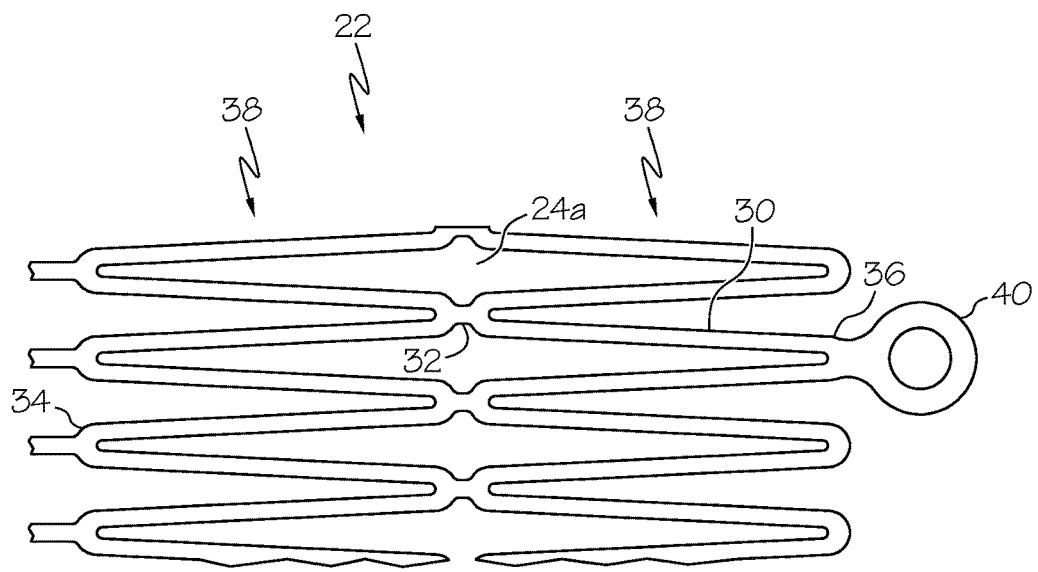
FIG. 6F is an enlarged portion of the stent in FIG. 6.

As can be seen from the figures, the barbs 50 do not form a part of the strut column 38 but instead extend from the strut column 38. In some embodiments, some, but not all, of the strut columns 38 in a region 18, 20, 22, of the stent have barbs 50 extending therefrom. For example, as shown in FIGS. 5 and 6, only two of the strut columns 38 of the middle region 20 have barbs 50 extending therefrom. In at least one embodiment, the strut column 38a of the middle region 20 does not have any barbs extending therefrom.

In some embodiments, the barb 50 extends from a peak 34 of a strut column 38, as shown for example in FIG. 2D. In other embodiments, the barb 50 extends from a valley 36 of a strut column 38, as shown for example in FIGS. 3 and 5-6. As shown in FIGS. 3 and 5-9 at least a portion of the barb 50 is positioned between, nested between, two circumferentially adjacent struts of a strut column 38 when the barb is in the unexpanded state. In at least one embodiment, the barbs 50 extend from the peak 34 or the valley 36 from which a connector extends. For example FIG. 5C shows a barb 50 that extends from a peak 34 from which a connector 32 extends where the barb 50 and the connector 32 extend in opposite directions. In at least one embodiment, the barb 50 extends from a chevron turn 35a. This is shown for example in FIG. 2. In still other embodiments, the barb 50 extends from a strut 30a of a strut column 38. This can be seen for example in FIG. 8. As shown in FIG. 8, the barb 50 extends from the side of the strut 30a.

Figure 10:
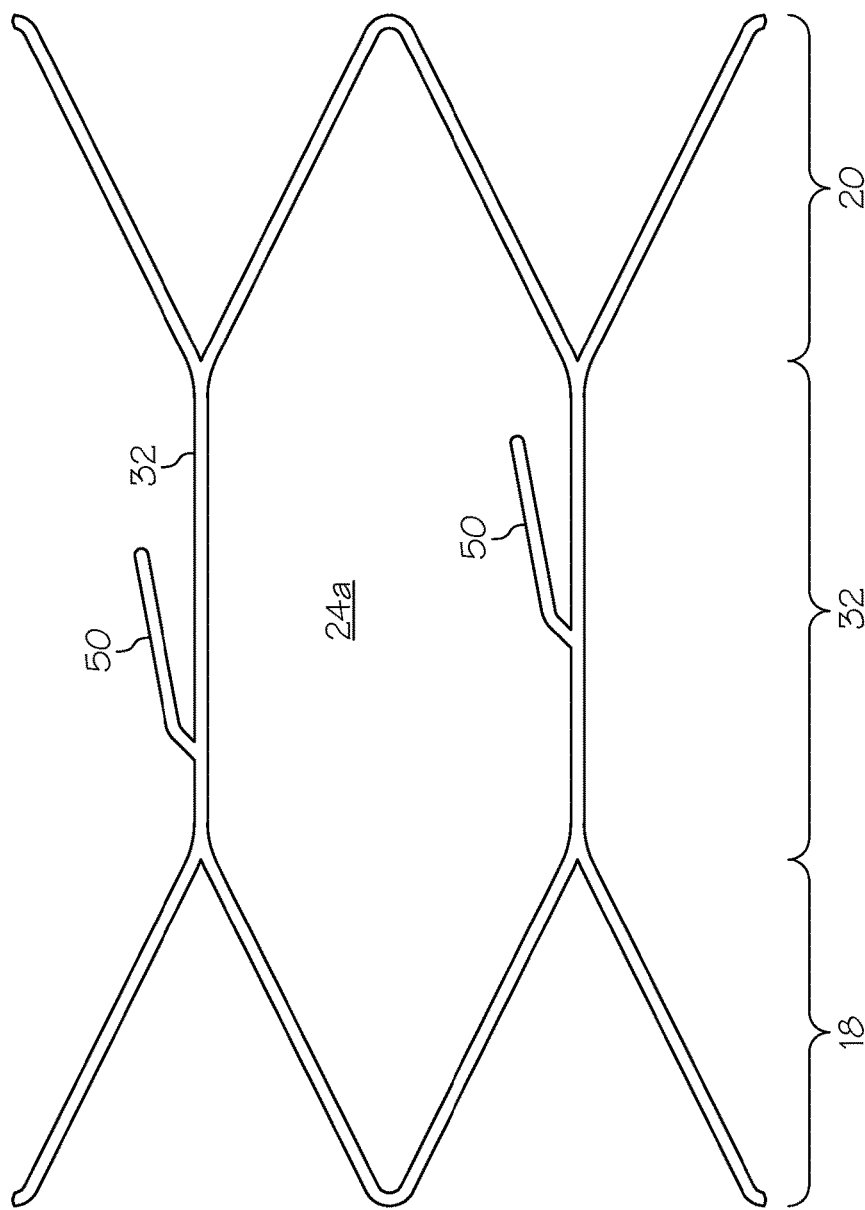

In at least one embodiment, a connector 32a has at least one barb 50 extending therefrom. In some embodiments, the connector 32a with a barb 50 extends between the middle region 20 to an end region 18, 22 of the stent 10. FIGS. 7 and 9-10 are examples of a stent pattern with connector regions 31 comprising connectors 32a with a barb 50.

FIGS. 7 and 9-12 show examples of a connector 32a with at least one barb 50 extending from the connector. In some embodiments, the barb 50 extends from two connectors. This can be seen for example in FIG. 7. As can be seen in FIG. 7, the end region 54 of the barb 50 has two legs 58 with each leg 58 extending from a connector 32 in a connector region 31. The legs 58 of the barb in FIG. 7 can be described as each extending from the side of a connector 32a. In other embodiments, the barb 50 extends from only one connector 32a. This can be seen for example in FIGS. 9-12. As shown in FIGS. 9-11, the barb 50 extends from the side of the connector 32a. As shown in FIG. 12, the barb 50 is within a cell 24 defined by the connector 32.

In at least one embodiment, the barb 50 has a length greater than the length of the struts 30. For example, as shown in FIG. 2, the barbs 50 extend from valley 36 to a tip region (indicated by cross-hatching in FIG. 2D) and the barbs 50 are longer than the struts 30 so that the free end/tip 51 of the barb 50 extends longitudinally beyond the turns 35 when the barb 50 is in the unexpanded state. The connectors 32 have a length that is greater than the length of the barb 50.

In at least one embodiment, each barb 50 extending from the same strut column 38 has the same configuration. For example, the barbs 50 extending from the strut columns 38 of the middle region in FIG. 2 have the same configuration. In some embodiments, the tips 51 of the barbs 50 on a stent 10 are directed to the same end 12, 14 of the stent 10. In one embodiment, a stent 10 with barbs 50 in an expanded state all facing the same direction prevent migration of the stent 10 after implantation into a body lumen but allows removal of the stent 10 from the body lumen. For example the barbs 50 of the stent 10 shown in FIGS. 2-3 all face the second end 14 of the stent 10.

In at least one embodiment, the stents 10 are made from superelastic Nitinol.

In at least one embodiment the at least a portion of the stent 10 is configured to include one or more mechanisms for the delivery of at least one agent. It is within the scope of the invention for the agent to be a therapeutic agent, hydrophilic. Often the agent will be in the form of a coating or other layer (or layers) of material placed on a surface region of the stent 10, which is adapted to be released over a period of time at the site of the stent's implantation or areas adjacent thereto. It is within the scope of the invention for the agent to be a therapeutic agent, a hydrophilic agent, or any combination thereof. In some embodiments, the therapeutic agent prevents mucous accumulation for airway stents or mineral buildup for stents used in the urinary tract. Without being bound by theory, in at least one embodiment, a stent 10 coated with a hydrophilic coating prevents the accumulation of mucus or biofilm. In one embodiment, the hydrophilic coating also includes an antimicrobial agent.

A therapeutic agent may be a drug or other pharmaceutical product such as non-genetic agents, genetic agents, cellular material etc., and combinations thereof. In some embodiments, the therapeutic agent is an antimicrobial agent. In one embodiment, the antimicrobial agent is silver. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The stent may also be partially or fully covered with a silicone elastomer or any other type of covering that prevents tumor or tissue ingrowth through at least some of the open cells. It is within the scope of the invention for the cover to be positioned on the inner surface of the stent, the outer surface of the stent, or on both the inner surface, the outer surface of the stent, an entire surface, portions of the surface, and combinations thereof.

B. Method of Fabrication/Method of Deployment

An exemplary method of fabricating and deploying a stent 10 as disclosed above includes at least some of the following steps:

Step: Form the as cut state of the stent.

The stents 10 may be created by methods including cutting or etching a design from a tubular stock or from a flat sheet which is subsequently rolled. Suitable techniques for cutting include lasers, electron discharge, and any other suitable technique which is known in the art or which is subsequently developed.

Cut a predetermined stent pattern comprising a plurality of barbs 50 in a tube of stent material to form a stent 10. In one embodiment, the pattern is cut using a laser. In another embodiment, the pattern is chemically or electrochemically etched. In some embodiments, the tube has a thickness ranging from 0.010 to 0.020 inches, an outer diameter ranging from 0.1 to 0.3 inches. In at least one embodiment, the tube is made of nitinol.

Step: Polish the stent 10 to remove metal slags. In some embodiments, the stent 10 has a thickness of about 0.09-0.019 inches after polishing.

Step: Form the parent state of the stent, the stent 10 is expanded to a desired final parent diameter. In some embodiments, the stent 10 is expanded in several steps until the desired final parent diameter is obtained. In one embodiment, the stent 10 is expanded on a shape mandrel.

Expand at least some of the barbs 50.

In at least one embodiment, the barbs 50, are expanded during the final expansion step of the stent 10. In some embodiments, a tube sized closely to the barb 50 is heated. In one embodiment, the tube is heated to a temperature of 450° C. to 550° C. Slide the tube over the barb 50 and keep tube over the barb 50 for a period of time to heat the barb. In some embodiments, the heated tube is placed over the barb 50 for one to five seconds. Then the tube is directed upward relative to the outer surface of the stent 10 to an angle greater than a desired angle for the barb 50 in an expanded configuration. In some embodiments, the desired angle for the barb 50 is approximately 30° to 60°. In one embodiment, the desired angle for the barb 50 is 45°. In some embodiments, the barbs are expanded up to 90°. Remove the tube from the barb 50 so that the barb material is air quenched and set into its expanded configuration. In some embodiments, the barb 50 has some recoil towards the outer surface of the stent 10.

In some embodiments, the last expansion mandrel includes a plurality of protrusions, where each protrusion is located under a barb and the protrusion is configured to expand the barb to set its position during heat treatment. If desired, provide the tip regions 52 of at least some of the barbs 50 with an angle relative to the rest of the barb 50. This can be achieved by shaping the protrusions and using an outside collar to bend the barb extremities.

Heat-treat the expanded stent 10.

Step: Provide at least some of the barbs 50 with a focal removal 56. In some embodiments, a laser removes a portion of the inner surface of the barb 50 to form the focal removal 56. Other suitable methods such as etching can be used to remove a portion of the inner surface of the barb 50 to form the focal removal 56. This step could be done at any time, e.g. on the tube itself, after cutting, or after the final expansion step of the stent 10.

Step: Provide the tip regions 52 of at least some of the barbs 50 with an angle relative to the rest of the barb 50. In one embodiment, a heated tube is slide over the tip region and the tip region is deformed into the desired direction and angle. This step is done after the expanded stent is heat-treated.

Step: Add a cover to the stent 10. Coverings for the stent are discussed above.

In some embodiments, the stent is placed on a mandrel, the stent/mandrel assembly is dipped in a silicone elastomer solution, the solvent is evaporated, and the elastomer is cured. Note that spraying may be used instead of dipping.

Step: Add a further coating. Coatings for the stent are discussed above.

Step: Load stent onto a stent delivery system.

In some embodiments, the angle of the barbs relative to the outer surface of the stent is less in the loaded state than in the parent state. Thus, the barb can be considered to be at a first angle relative to the outer surface of the stent when the stent is in the parent state, and at a second angle relative to the outer surface of the stent when the stent is in the loaded state, where the first angle is greater than the second angle.

Step: Deliver the stent 10 with at least one barb 50 to a desired location in a body lumen using a delivery system. It is within the scope of the invention for any suitable delivery system to be used to delivery a stent as described herein.

In at least one embodiment, the stent 10 is delivered to a portion of the respiratory system. In some embodiments, the stent 10 is delivered to the trachea. In other embodiments, the stent 10 is delivered to the bronchi.

Step: Expand stent 10.

stent 10 self expands because of its superelasicity.

Step: Expand at least some of the barbs 50.

the barbs self-expand to a second angle upon removal of the stress applied by the delivery system because of its superelasticity.

The following statements characterize at least one of the embodiments described above:

Statement 1. A stent having an as cut state and a parent state, the stent comprising:
 a first end;
 a first end region, the first end region comprising a first strut column, a second strut column, and a plurality of peak to valley connectors extending between the first strut column and the second strut column;
 a middle region comprising:
  a plurality of barbs, each barb having an unexpanded state and an expanded state, each barb being in the unexpanded state when the stent is in the as cut state;
  a plurality of strut columns comprising a plurality of struts; interconnected by turns, the plurality of strut columns comprising a plurality of first strut columns;
  a plurality of peak to peak connectors extending between adjacent strut columns;
  each barb extending from one of the plurality of first strut columns;
 a second end region, the second end region comprising a first strut column, a second strut column, and a plurality of peak to valley connectors extending between the first strut column and the second strut column;
 a plurality of first peak to valley connectors extending between the first end region and the middle region;
 a plurality of second peak to valley connectors extending between the second end region and the middle region; and
 a second end;
 at least some of the barbs being in the expanded state when the stent is in the parent state.

Statement 2. A stent having an as cut state and a parent state, the stent comprising:
 a first end;
 a first end region, the first end region comprising a first strut column, a second strut column, a plurality of barbs, and a plurality of peak to valley connectors connecting the first strut column and the second strut column;
a middle region, the middle region comprising a plurality of strut columns, adjacent strut columns connected by a plurality of peak to peak connectors;
a second end region, the second end region comprising a first strut column, a second strut column, a plurality of barbs, and a plurality of peak to valley connectors connecting the first strut column and the second strut column;
a plurality of first peak to valley connectors engaging the first end region and the middle region;
a plurality of second peak to valley connectors engaging the second end region and the middle region; and
a second end;
at least some of the barbs being in the expanded state when the stent is in the parent state.

Statement 3. A stent having an as cut state and a parent state, the stent comprising:
a first end;
a first end region, the first end region comprising a first strut column, a second strut column, and a plurality of peak to valley connectors connecting the first strut column and the second strut column;
a middle region, the middle region comprising a plurality of strut columns, adjacent strut columns connected by a plurality of peak to peak connectors;
a second end region, the second end region comprising a first strut column, a second strut column, and a plurality of peak to valley connectors connecting the first strut column and the second strut column;
a plurality of first peak to valley connectors engaging the first end region and the middle region, some of the first peak to valley connectors having a first barb extending therefrom;
a plurality of second peak to valley connectors engaging the second end region and the middle region, some of the second peak to valley connectors having a second barb extending therefrom; and
a second end;
at least some of the barbs being in the expanded state when the stent is in the parent state.

Statement 4. The stent of Statements 1-3, wherein when the stent is in the parent state, the middle region has a diameter that is smaller than a diameter of the first end region and smaller than a diameter of the second end region.

Statement 5. The stent of Statements 1-4, the barb in the expanded state being at a an angle relative to an outer surface of the stent, the angle being about 30° to about 60°.

Statement 6. The stent of Statements 1-5, each barb having a focal removal.

Statement 7. The stent of Statements 1-6, each barb having a bent tip region.

Statement 8. The stent of Statements 1-7, each barb having a variable width, a variable thickness, or a variable width and a variable thickness along a length of the barb.

Statement 9. The stent of Statements 1-8, the free end of at least one of the at least one barb being circumferentially offset from a turn from which the at least one of the at least one barb extends.

Statement 10. The stent of Statements 1-9, each barb facing towards the first end of the stent.

Statement 11. The stent of Statements 1-10, each barb nesting between two adjacent struts of a strut column.

Statement 12. The stent of Statements 1-11, some of the plurality of barbs facing the first end of the stent and others of the plurality of barbs facing the second end of the stent.

Statement 13. The stent of Statements 2 and 3-12, some of the plurality of barbs extending from a strut of the first strut column of the first end region and others of the plurality of barbs extending from a strut of the second strut column of the second end region.

Statement 14. The stent of Statements 1-2 and 4-12, each barb extending from a valley, each barb having a barb length greater than a strut length.

Statement 15. The stent of Statements 1-2 and 4-12, each barb extending from a peak and nesting between two struts of an adjacent strut column.

Statement 16. The stent of Statements 1-15, at least some of the barbs having an end region a width greater than the body of the barb.

Statement 17. The stent of Statements 1-16, the middle region of the stent further comprising a second strut column comprising a plurality of struts interconnected by turns, the second strut column forming an end of the middle region, the second strut column having a different configuration than a configuration of the first strut columns, wherein no barbs extend from the second strut column.

Statement 18. The stent of Statement 17, the turns of the first strut columns comprising first turns and second turns, the first turns having a smaller circumferential width than the second turns, the turns of the second strut columns comprising only first turns.

Statement 19. The stent of Statements 1-18, each first strut column having a first end facing the first end of the stent and a second end facing the second end of the stent, the turns of each first strut column comprising first turns and second turns, the first end turns having a smaller width than the second turns,
the first end of the first strut columns comprising first turns and second turns forming a repeating first pattern, the first pattern being first turn-second turn-second turn-second turn;
the second end of the first strut column comprising only first turns.

Statement 20. The stent of Statements 1-19, each first strut columns having a first end facing the first end of the stent and a second end facing the second end of the stent, the turns of each first strut column comprising first turns and second turns, the first end turns having a smaller width than the second turns,
the first end of the first strut columns comprising first turns and second turns forming a repeating first pattern, the first pattern being first turn-second turn-first turn-second turn;
the second end of the first strut column comprising only first turns.

Statement 21. The stent of Statements 1-20, the plurality of first peak to valley connectors and the plurality of second peak to valley connectors being at an angle to an outer surface of the middle region when the stent is in the parent state.

Statement 22. The stent of Statements 1-21, the first and second end regions each defining a plurality of closed cells.

Statement 23. The stent of Statements 1-22, the plurality of first peak to valley connectors extending between each turn of a strut column forming an end of the first end region and each turn of a strut column forming an end of the middle region, and the plurality of second peak to valley connectors extending between each turn of a strut column forming an end of the second end region and each turn of a strut column forming another end of the middle region.

Statement 24. The stent of Statements 1-23, further comprising a cover attached to the stent.

Statement 25. The stent of Statements 1-24, wherein the stent is made of a material having superelastic properties.

Statement 26. The stent of Statements 1-24, wherein the stent is made of a material having shape memory properties.

Statement 27. A method of deploying the stent of Statements 1-26, comprising:
  providing the stent of Statements 1-26;
  delivering the stent to a desired location in a body lumen; and
  expanding the stent.

Statement 28. The method of Statement 27, wherein at least some of the barbs are at an angle of 30° to about 60° relative to an outer surface of the middle region of the stent Statement 29. A method of making the stent of Statements 1-26 comprising:
  forming a pattern in a tube of stent material to make the stent of Statements 1-26, the tube having a first end and a second end.

Statement 30. The method of Statement 29, further comprising polishing the stent after the pattern has been formed in the tube.

Statement 31. The method of Statements 29-30, the pattern being formed in the tube by a laser.

Statement 32. The method of Statements 27-31, further comprising attaching a cover to the stent.

Statement 33. The method of Statements 27-32, wherein the stent material is nitinol, the method further comprising expanding the stent to a desired final diameter.

Statement 34. The method of Statement 33, the method further comprising expanding at least some of the barbs.

Statement 35. The method of Statement 34, wherein expanding at least some of the barbs comprises:
  heating a tube, the tube being sized to cover the barb;
  sliding the heated tube over the barb, the heated tube heating the barb, after the barb is heated, moving the tube to an angle greater than a desired angle for the barb in the expanded configuration; and
  removing the tube from the barb.

Statement 36. The method of Statement 35, wherein the tube is heated to a temperature from 450° C. to 550° C.

Statement 37. The method of Statements 27-36, wherein the stent is expanded in several steps until the desired final diameter is obtained.

Statement 39. The method of Statements 27-37, wherein the stent is expanded on a shape mandrel.

Statement 40. The method of Statements 35, wherein the desired angle is approximately 30° to 60°.

Statement 41. The method of Statements 27-40, further comprising heat-treating.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent having an as cut state and a parent state, the stent comprising:
  a first end;
  a first end region, the first end region comprising a first strut column, a second strut column, and a plurality of peak to valley connectors connecting the first and second strut columns of the first end region;
  a middle region, the middle region comprising:
    a plurality of strut columns, each strut column comprising a plurality of struts interconnected by turns, the plurality of strut columns comprising
      a plurality of first strut columns having an axial length defined between the turns;
    a plurality of peak to peak connectors extending between and interconnecting adjacent first strut columns of the middle region;
    at least one barb, each barb extending from a peak of one of the plurality of first strut columns of the middle region toward a peak of an adjacent first strut column of the middle region and to a free tip of the barb, each barb having an unexpanded state and an expanded state, each barb being in the unexpanded state when the stent is in the as cut state, at least one barb being in the expanded state when the stent is in the parent state, each barb in the expanded state being at an angle relative to an outer surface of the stent, wherein when the stent is in the as cut state, a distance from the free tip of the barb to the peak of the one of plurality of first strut columns of the middle region that the barb extends from is less than a distance from the peak of the adjacent first strut column of the middle region to the peak of the first strut column of the middle region that the barb extends from:
  a second end region, the second end region comprising a first strut column, a second strut column, and a plurality of peak to valley connectors connecting the first and second strut columns of the second end region;
  a plurality of first peak to valley connectors engaging the first end region and the middle region;
  a plurality of second peak to valley connectors engaging the second end region and the middle region; and
  a second end;
  wherein when the stent is in the parent state, the middle region has a diameter that is smaller than a diameter of the first end region and smaller than a diameter of the second end region.

2. The stent of claim 1, each barb of the at least one barb having a focal removal, a bent tip region, or a focal removal and a bent tip region.

3. The stent of claim 1, the middle region of the stent further comprising a second strut column, the second strut column forming an end of the middle region, the plurality of first strut columns forming another end of the middle region, the second strut column having a different configuration than a configuration of the plurality of first strut columns, the second strut column having no barbs extending therefrom.

4. The stent of claim 3, wherein the turns of the plurality of strut columns of the middle region comprise first turns and second turns, the first turns having a smaller circumferential width than the second turns, the turns of the second strut column comprising only first turns.

5. The stent of claim 1, each first strut column of the plurality of first strut columns of the middle region having a first end facing the first end of the stent and a second end facing the second end of the stent, the turns of each of the plurality of first strut columns of the middle region comprising first turns and second turns, the first turns having a smaller circumferential width than the second turns,
the first end of each first strut column of the plurality of first strut columns of the middle region comprising the first turns and second turns forming a first pattern repeating along each first strut column of the plurality of first strut columns of the middle region, the first pattern being first turn-second turn-second turn-second turn;
the second end of each first strut column of the plurality of first strut columns of the middle region comprising only first turns;
the plurality of strut columns of the middle region further comprising a second strut column of the middle region comprising only first turns.

6. The stent of claim 1, each first strut column of the plurality of first strut columns of the middle region having a first end facing the first end of the stent and a second end facing the second end of the stent, the turns of each of the plurality of first strut columns of the middle region comprising first turns and second turns, the first turns having a smaller circumferential width than the second turns,
the first end of each of the first strut columns of the plurality of first strut columns of the middle region comprising the first turns and second turns forming a first pattern repeating along each first strut column of the plurality of first strut columns of the middle region, the first pattern being first turn-second turn-first turn-second turn;
the second end of each first strut column of the plurality of first strut columns of the middle region comprising only first turns;
the plurality of strut columns of the middle region further comprising a second strut column of the middle region comprising only first turns.

7. The stent of claim 1, the plurality of first peak to valley connectors and the plurality of second peak to valley connectors being at an angle to an outer surface of the middle region when the stent is in the parent state.

8. The stent of claim 1, the plurality of first peak to valley connectors extending between a strut column forming an end of the first end region and a strut column forming an end of the middle region, and the plurality of second peak to valley connectors extending between a strut column forming an end of the second end region and a strut column forming another end of the middle region.

9. A stent having an as cut state and a parent state, the stent comprising:
a first end;
a first end region, the first end region comprising a first strut column, a second strut column, and a plurality of peak to valley connectors connecting the first strut column and the second strut column;
a middle region, the middle region comprising
a plurality of middle strut columns arranged in phase with each other, adjacent middle strut columns connected by a plurality of peak to peak connectors, and
a plurality of barbs each extending axially from a peak of one of the plurality of middle strut columns toward a peak of an adjacent middle strut column to a free tip of the barb having an axial length measured therebetween;
a second end region, the second end region comprising a first strut column, a second strut column, and a plurality of peak to valley connectors connecting the first strut column and the second strut column;
a plurality of first peak to valley connectors engaging the first end region and the middle region;
a plurality of second peak to valley connectors engaging the second end region and the middle region; and
a second end;
wherein when the stent is in the parent state, the middle region has a diameter that is smaller than a diameter of the first end region and smaller than a diameter of the second end region;
wherein each strut column of the plurality of middle strut columns comprises a plurality of struts interconnected by turns and at least some of the plurality of barbs being in an expanded state when the stent is in the parent state, the plurality of barbs in the expanded state being at an angle relative to an outer surface of the stent;
wherein each strut column of the plurality of middle strut columns has an axial length defined between the turns, and wherein when the stent is in the as cut state, the axial length of each barb is less than an axial distance from the peak of the adjacent middle strut column to the middle strut column that the one of the plurality of middle strut columns barb extends from.

10. The stent of claim 9, one of the plurality of middle strut columns includes at least one of the plurality of barbs extending therefrom and another of the plurality of middle strut columns includes at least one of the plurality of barbs extending therefrom.

11. The stent of claim 9, the plurality of middle strut columns comprising a plurality of first middle strut columns each having a first configuration and a second middle strut column having a second configuration, the second strut column forming an end of the middle region, the first configuration different than the second configuration.

12. The stent of claim 11, each first middle strut column of the plurality of first middle strut columns having a first end facing the first end of the stent and a second end facing the second end of the stent, the turns of each middle strut column of the plurality of middle strut columns comprising first turns and second turns, the first turns having a smaller circumferential width than the second turns,
the first end of each first middle strut columns comprising first turns and second turns forming a first pattern repeating along each first middle strut column, the first pattern being first turn-second turn-first turn-second turn;
the second end of each first middle strut column comprising only first turns;

the second middle strut column comprising only first turns.

\* \* \* \* \*